US009895813B2

(12) United States Patent
Blumenkranz et al.

(10) Patent No.: US 9,895,813 B2
(45) Date of Patent: Feb. 20, 2018

(54) FORCE AND TORQUE SENSING IN A SURGICAL ROBOT SETUP ARM

(75) Inventors: Stephen J Blumenkranz, Redwood City, CA (US); Guiseppe M Prisco, Mountain View, CA (US); Simon Peter DiMaio, Sunnyvale, CA (US); Gregory William Dachs, II, Sunnyvale, CA (US); Hanifa Dostmohamed, West St. Paul (CA); Christopher J Hasser, Los Altos, CA (US); Gary S Guthart, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1130 days.

(21) Appl. No.: 12/060,004

(22) Filed: Mar. 31, 2008

(65) Prior Publication Data
US 2009/0248038 A1 Oct. 1, 2009

(51) Int. Cl.
*B25J 13/08* (2006.01)
*A61B 34/00* (2016.01)
*A61B 34/30* (2016.01)
*A61B 34/37* (2016.01)
*A61B 17/00* (2006.01)
*A61B 90/00* (2016.01)
(Continued)

(52) U.S. Cl.
CPC ............. *B25J 13/085* (2013.01); *A61B 34/30* (2016.02); *A61B 34/37* (2016.02); *A61B 34/71* (2016.02); *A61B 46/10* (2016.02); *A61B 90/361* (2016.02); *A61B 90/50* (2016.02); *A61B 2017/00477* (2013.01); *A61B 2034/305* (2016.02); *A61B 2090/064* (2016.02); *G05B 2219/40582* (2013.01)

(58) Field of Classification Search
CPC ...... A61B 2019/2223; A61B 2019/464; G05B 2219/40599; G05B 2219/40582; G05B 2219/42221
USPC ............... 600/587, 595; 318/568.11, 568.21; 901/8–9, 33–34, 48
See application file for complete search history.

(56) References Cited

U.S. PATENT DOCUMENTS

| | | | |
|---|---|---|---|
| 4,768,918 A * | 9/1988 | Gorman et al. | ............... 414/719 |
| 4,807,486 A | 2/1989 | Akeel | |
| 5,038,089 A | 8/1991 | Szakaly | |

(Continued)

FOREIGN PATENT DOCUMENTS

| FR | 2693397 A1 | 1/1994 |
|---|---|---|
| JP | 2002530209 A | 9/2002 |

(Continued)

OTHER PUBLICATIONS

PCT/US09/38160 International Search Report and Written Opinion of the International Searching Authority, dated Sep. 3, 2009, 13 pages.

(Continued)

*Primary Examiner* — Rene Towa
*Assistant Examiner* — H. Q. Nguyen

(57) ABSTRACT

An apparatus, system, and method for improving force and torque sensing and feedback to the surgeon performing a telerobotic surgery are provided. In one embodiment, a robotic surgical manipulator system, a robotic surgical system, and a method for improved sensing of forces on a robotic surgical instrument and/or manipulator arm are disclosed.

27 Claims, 19 Drawing Sheets

(51) Int. Cl.
*A61B 90/50* (2016.01)
*A61B 46/10* (2016.01)

(56) References Cited

U.S. PATENT DOCUMENTS

| | | |
|---|---|---|
| 5,130,632 A | 7/1992 | Ezawa et al. |
| 5,178,431 A | 1/1993 | Voellmer |
| 5,631,973 A | 5/1997 | Green |
| 5,767,648 A * | 6/1998 | Morel et al. ............... 318/568.1 |
| 5,807,377 A | 9/1998 | Madhani et al. |
| 5,901,613 A * | 5/1999 | Forslund ................... 74/490.03 |
| 6,246,200 B1 | 6/2001 | Blumenkranz et al. |
| 6,331,181 B1 | 12/2001 | Tierney et al. |
| 6,371,952 B1 | 4/2002 | Madhani et al. |
| 6,377,011 B1 | 4/2002 | Ben-Ur |
| 6,451,027 B1 | 9/2002 | Cooper |
| 6,491,701 B2 | 12/2002 | Tierney et al. |
| 6,493,608 B1 | 12/2002 | Niemeyer |
| 6,574,355 B2 | 6/2003 | Green |
| 6,587,750 B2 * | 7/2003 | Gerbi et al. ................. 700/245 |
| 6,676,684 B1 | 1/2004 | Morley et al. |
| 6,770,081 B1 | 8/2004 | Cooper et al. |
| 6,783,524 B2 | 8/2004 | Anderson et al. |
| 6,786,896 B1 | 9/2004 | Madhani |
| 6,817,974 B2 | 11/2004 | Cooper et al. |
| 6,835,173 B2 | 12/2004 | Couvillon, Jr. |
| 6,866,671 B2 | 3/2005 | Tierney et al. |
| 6,879,880 B2 | 4/2005 | Nowlin et al. |
| 6,902,560 B1 | 6/2005 | Morley et al. |
| 6,936,042 B2 | 8/2005 | Wallace et al. |
| 7,250,028 B2 | 7/2007 | Julian et al. |
| 2001/0022112 A1* | 9/2001 | Bayer et al. ............... 74/490.01 |
| 2005/0200324 A1 | 9/2005 | Guthart et al. |
| 2006/0161136 A1 | 7/2006 | Anderson et al. |
| 2006/0161137 A1 | 7/2006 | Orban, III et al. |
| 2006/0161138 A1 | 7/2006 | Orban, III et al. |
| 2006/0235436 A1 | 10/2006 | Anderson et al. |
| 2006/0276882 A1* | 12/2006 | Case ............................. A61F 2/07 623/1.24 |
| 2007/0018958 A1* | 1/2007 | Tavakoli .................. B25J 13/02 345/161 |
| 2007/0119274 A1 | 5/2007 | Devengenzo et al. |
| 2007/0137371 A1 | 6/2007 | Devengenzo et al. |
| 2007/0137372 A1 | 6/2007 | Devengenzo et al. |
| 2007/0142823 A1* | 6/2007 | Prisco et al. ...................... 606/1 |
| 2007/0142824 A1 | 6/2007 | Devengenzo et al. |
| 2007/0142968 A1* | 6/2007 | Prisco et al. ................... 700/245 |
| 2007/0151390 A1 | 7/2007 | Blumenkranz et al. |
| 2007/0151391 A1 | 7/2007 | Larkin et al. |
| 2007/0156019 A1 | 7/2007 | Larkin et al. |
| 2008/0065111 A1 | 3/2008 | Blumenkranz et al. |
| 2009/0259412 A1* | 10/2009 | Brogardh .............. B25J 9/1633 702/41 |

FOREIGN PATENT DOCUMENTS

| | | |
|---|---|---|
| WO | WO-9740435 A2 | 10/1997 |
| WO | WO 2007096322 * | 8/2007 |
| WO | 2007120329 A2 | 10/2007 |

OTHER PUBLICATIONS

Vertut, Jean et al., Robot Technology: Teleoperation and Robotics Evolution and Development, 1986, vol. 3A, 332 pages, English translation Prentice-Hall, Inc., Inglewood Cliffs, NJ, USA.
U.S. Appl. No. 11/758,772, filed Dec. 18, 2007.
F. Geggard, et al., On the use of a base force/torque sensor in teleoperation, Proceedings of the 2000 IEEE Int'l Conference on Robotics & Automation, Apr. 2000, pp. 2677-2683, San Francisco, California, USA.
F.Cepolina, R C Michelini, Review of robotic fixtures for minimally invasive surgery, Int'l J. Medical Robotics and Computer Assisted Surgery, vol. 1, pp. 43-63, Apr. 2004.
U.S. Appl. No. 60/755,108, filed Dec. 30, 2005.
U.S. Appl. No. 60/755,157, filed Dec. 30, 2005.

* cited by examiner

FORCE AND TORQUE SENSING IN A SURGICAL ROBOT SETUP ARM

CROSS-REFERENCE TO RELATED APPLICATIONS AND PATENTS

This application is related to U.S. Provisional Application No. 60/755,108 filed Dec. 30, 2005, U.S. Provisional Application 60/755,157 filed Dec. 30, 2005, U.S. application Ser. No. 11/958,772 filed Dec. 18, 2007, U.S. application Ser. No. 11/864,974 filed Sep. 29, 2007, U.S. application Ser. No. 11/553,303 filed Oct. 26, 2006, U.S. patent application Ser. No. 11/537,241 filed Sep. 29, 2006, U.S. patent application Ser. No. 11/093,372 filed Mar. 30, 2005, and U.S. Pat. Nos. 6,936,042, 6,902,560, 6,879,880, 6,866,671, 6,817,974, 6,783,524, 6,676,684, 6,371,952, 6,331,181, and 5,807,377, the full disclosures of which are incorporated by reference herein for all purposes.

TECHNICAL FIELD

The present invention relates generally to surgical robot systems and, more particularly, to a system and method for sensing forces applied to a surgical instrument and/or a surgical robotic manipulator.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves inserted through incisions into a body cavity, such as the patient's abdomen. Depending on the surgical procedure, there are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, or dissecting, cauterizing or coagulating tissue. A surgeon may employ a large number of different surgical instruments/tools during a procedure.

This new method of performing telerobotic surgery through remote manipulation has created many new challenges. One such challenge is providing the surgeon with the ability to accurately "feel" the tissue that is being manipulated by the surgical instrument via the robotic manipulator. The surgeon must rely on indications of the forces applied by the instruments or sutures. It is desirable to sense the forces and torques applied to the tip of the instrument, such as an end effector (e.g., jaws, grasper, blades, etc.) of robotic endoscopic surgical instruments, in order to feed the forces and torques back to the surgeon user through the system hand controls or by other means such as visual display or audible tone.

One device for this purpose from the laboratory of G. Hirzinger at DLR Institute of Robotics and Mechatronics is described in "Review of Fixtures for Low-Invasiveness Surgery" by F. Cepolina and R C Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

Another problem has been fitting and positioning the necessary wires for mechanical actuation of end effectors in as small a space as possible because relatively small instruments are typically desirable for performing surgery.

Yet another problem has been sensing forces and torques on the manipulator arm itself (e.g., inside and/or outside the patient) amid mechanical vibrations that may result from compliance of the manipulator arm or its support.

What is needed, therefore, are improved telerobotic systems and methods for remotely controlling surgical instruments at a surgical site on/in a patient. In particular, these systems and methods should be configured to provide accurate feedback of forces and torques to the surgeon to improve user awareness and control of the instruments and manipulator.

SUMMARY

The present invention provides an apparatus, system, and method for improving force and torque feedback to and sensing by the surgeon performing a telerobotic surgery. In particular, a robotic surgical manipulator, a robotic surgical system, and a method for improved sensing of forces on a robotic surgical instrument and/or the manipulator itself are disclosed.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1A:
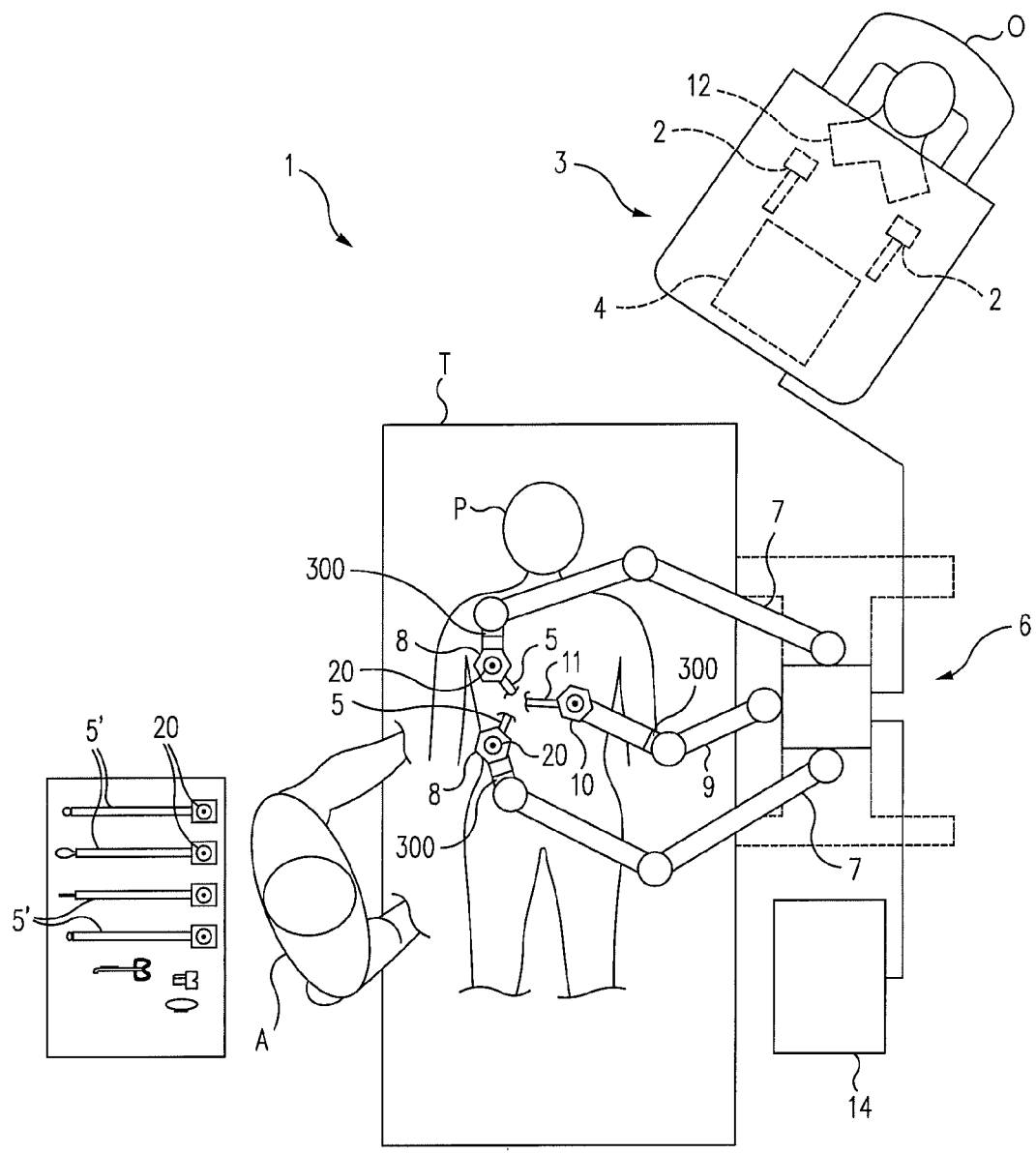
FIG. 1A is a plan view of a robotic surgical system in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces while performing robotically-assisted surgical procedures on a patient, particularly including open surgical procedures, neurosurgical procedures, and endoscopic procedures, such as laparoscopy, arthroscopy, thoracoscopy, and the like. The system and method of the present invention are particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master having at least six or more degrees of freedom (e.g., 3 degrees of freedom for position and 3 degrees of freedom for orientation) to form a telepresence system with force reflection or display. A description of a suitable slave-master system can be found in U.S. Pat. No. 6,574,355, the complete disclosure of which is incorporated herein by reference for all purposes.

A robotic system of the present invention generally includes one or more surgical manipulator assemblies mounted to or near an operating table and a master control assembly for allowing a surgeon to view the surgical site and to control the manipulator assemblies. The system will also include one or more viewing scope assemblies and a plurality of surgical instruments adapted for being removably coupled to the manipulator assemblies (discussed in more detail below). The robotic system includes at least two manipulator assemblies and preferably at least three manipulator assemblies. The exact number of manipulator assemblies will depend on the surgical procedure and the space constraints within the operating room, among other factors. As discussed in detail below, one of the assemblies will typically operate a viewing scope assembly (e.g., in endoscopic procedures) for viewing the surgical site, while the other manipulator assemblies operate surgical instruments for performing various procedures on a patient.

The control assembly may be located at a surgeon's console which is usually located in the same room as the operating table so that the surgeon may speak to his/her assistant(s) and directly monitor the operating procedure. However, it should be understood that the surgeon can be located in a different room or a completely different building from the patient. The master control assembly generally includes a support, a monitor for displaying an image of the surgical site to the surgeon, and one or more master(s) for controlling the manipulator assemblies. Master(s) may include a variety of input devices, such as hand-held wrist gimbals, joysticks, gloves, trigger-guns, hand-operated controllers, voice recognition devices, or the like. Preferably, master(s) will be provided with the same degrees of freedom as the associated surgical instrument assemblies to provide the surgeon with telepresence, the perception that the surgeon is immediately adjacent to and immersed in the surgical site, and intuitiveness, the perception that the master(s) are integral with the instruments so that the surgeon has a strong sense of directly and intuitively controlling instruments as if they are part of his or her hands. Position, force, and tactile feedback sensors may also be employed on instrument assemblies to transmit signals that may be used to represent position, force, and tactile sensations from the surgical instrument back to the surgeon's hands as he/she operates the telerobotic system. One suitable system and method for providing telepresence to the operator is described in U.S. Pat. No. 6,574,355, which has previously been incorporated herein by reference.

The monitor will be suitably coupled to the viewing scope assembly such that an image of the surgical site is provided adjacent the surgeon's hands on the surgeon console. Preferably, the monitor will display an image on a display that is oriented so that the surgeon feels that he or she is actually looking directly down onto the operating site. To that end, an image of the surgical instrument appears to be located substantially where the operator's hands are located even though the observation points (i.e., the endoscope or viewing camera) may not be from the point of view of the image. In addition, the real-time image is preferably transformed into a stereo image such that the operator can manipulate the end effector and the hand control as if viewing the workspace in substantially true presence. By true presence, it is meant that the presentation of an image is a true stereo image simulating the viewpoint of an operator that is physically manipulating the surgical instruments. Thus, a controller (not shown) transforms the coordinates of the surgical instruments to a perceived position so that the stereo image is the image that one would see if, for example, the camera or endoscope was located directly behind the surgical instruments. A suitable coordinate transformation system for providing this virtual image is described in U.S. patent application Ser. No. 08/239,086, filed May 5, 1994, now U.S. Pat. No. 5,631,973, the complete disclosure of which is incorporated herein by reference for all purposes.

A servo control is provided for transferring the mechanical motion of masters to the manipulator assemblies. The servo control may be separate from, or integral with, the manipulator assemblies. The servo control may provide force and torque feedback from the surgical instruments to the hand-operated masters. In addition, the servo control may include a safety monitoring controller to safely halt system operation, or at least inhibit all robot motion, in response to recognized undesirable conditions (e.g., exertion of excessive force on the patient, mismatched encoder readings, etc.). In one example, the servo control preferably has a servo bandwidth with a 3 dB cut off frequency of at least 10 Hz so that the system can quickly and accurately respond to the rapid hand motions used by the surgeon and yet filter out undesirable surgeon hand tremors. To operate effectively with this system, the manipulator assemblies have a relatively low inertia, and the drive motors have relatively low ratio gear or pulley couplings. Any suitable conventional or specialized servo control may be used in the practice of the present invention.

Figure 1B:
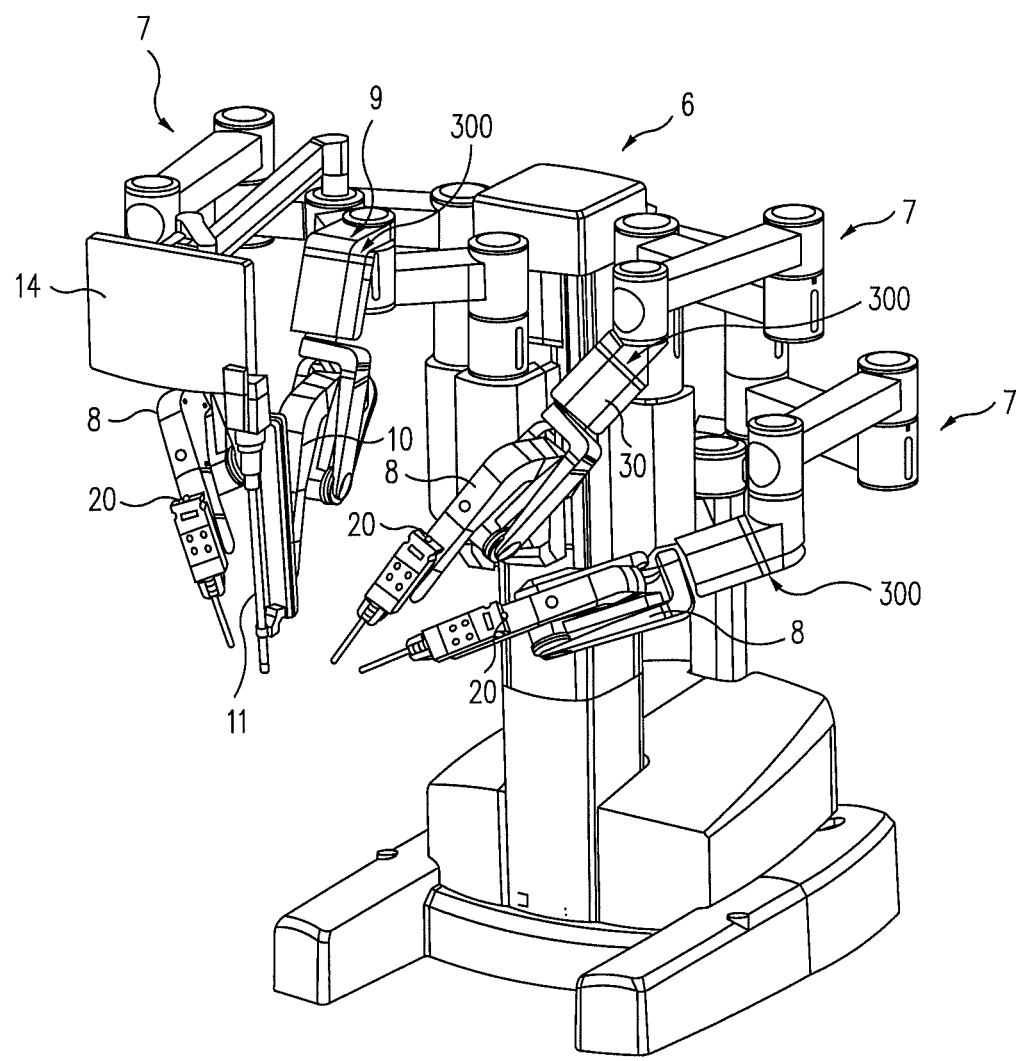
FIGS. 1B and 1C illustrate a perspective view and a front view, respectively, of an embodiment of a manipulator system, including a force sensor at the base of a manipulator arm and positioning linkages or set up joints which allow a patient side robotic manipulator and/or an endoscope or camera robotic manipulator to be pre-configured for surgery.
Figure 1C:
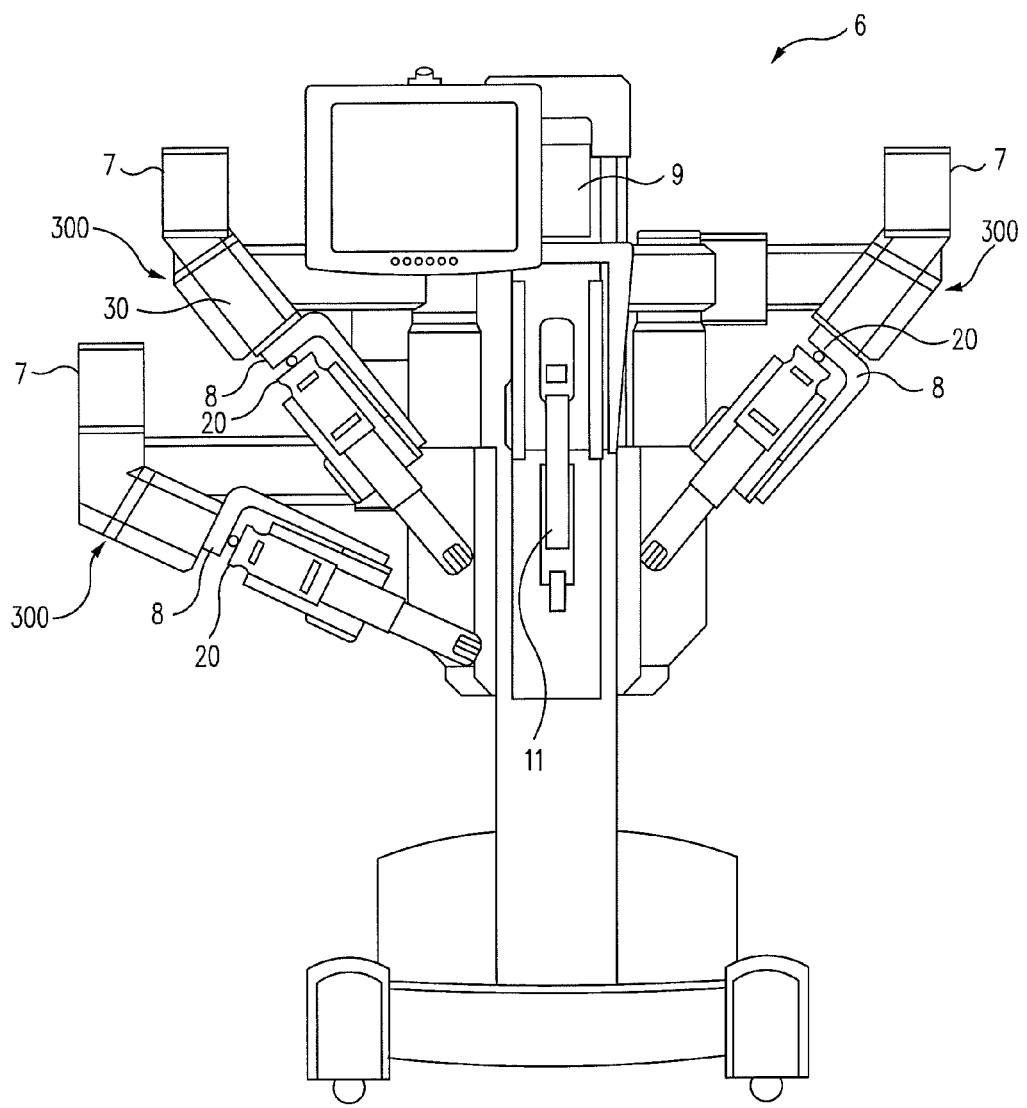

Referring now to the drawings in detail, wherein like numerals indicate like elements, FIGS. 1A-1C illustrate components of a robotic surgical system 1 for performing minimally invasive robotic surgery in accordance with an embodiment of the present invention. System 1 is similar to that described in more detail in U.S. Pat. No. 6,246,200, the full disclosure of which is incorporated herein by reference.

A system operator O (generally a surgeon) performs a minimally invasive surgical procedure on a patient P lying on an operating table T. The system operator O sees images presented by display 12 and manipulates one or more input devices or masters 2 at a surgeon's console 3. In response to the surgeon's input commands, a computer processor 4 of console 3 directs movement of surgical instruments or tools 5, effecting servomechanical movement of the instruments via a robotic patient-side manipulator system 6 (a cart-based system in this example) including joints, linkages, and manipulator arms each having a telescopic insertion axis. In one embodiment, processor 4 correlates the movement of the end effectors of tools 5 so that the motions of the end effectors follow the movements of the input devices in the hands of the system operator O.

Processor 4 will typically include data processing hardware and software, with the software typically comprising machine-readable code. The machine-readable code will embody software programming instructions to implement some or all of the methods described herein. While processor 4 is shown as a single block in the simplified schematic of FIG. 1, the processor may comprise a number of data processing circuits, with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein.

In one example, manipulator system 6 includes at least four robotic manipulator assemblies. Three setup linkages 7 (mounted at the sides of the cart in this example) support and position manipulators 8 with linkages 7 in general supporting a base of the manipulators 8 at a fixed location during at least a portion of the surgical procedure. Manipulators 8 move surgical tools 5 for robotic manipulation of tissues. One additional linkage 9 (mounted at the center of the cart in this example) supports and positions manipulator 10 which controls the motion of an endoscope/camera probe 11 to capture an image (preferably stereoscopic) of the internal surgical site. The fixable portion of positioning linkages 7, 9 of the patient-side system is sometimes referred to herein as a "setup arm"

Assistant A assists in pre-positioning manipulators 8 and 10 relative to patient P using setup linkage arms 7 and 9, respectively; in swapping tools 5 from one or more of the surgical manipulators for alternative surgical tools or instruments 5'; in operating related non-robotic medical instruments and equipment; in manually moving a manipulator assembly so that the associated tool accesses the internal surgical site through a different aperture, and the like.

In general terms, the linkages 7, 9 are used primarily during setup of patient-side manipulator system 6, and typically remain in a fixed configuration during at least a portion of a surgical procedure. Manipulators 8, 10 each comprise a driven linkage which is actively articulated under the direction of surgeon's console 3. Although one or more of the joints of the setup arm may optionally be driven and robotically controlled, at least some of the setup arm joints may be configured for manual positioning by assistant A.

In accordance with an embodiment of the present invention, a force/torque (F/T) sensor 300 is operably coupled between the base of a manipulator (e.g., manipulator 8 or 10) and outboard the respectively coupled setup linkage (e.g., linkage 7 or 9). In one example, one side of F/T sensor 300 is operably attached to the end of a passive setup arm linkage and another side of F/T sensor 300 is operably attached to the base of a servo-actuated manipulator. In another example, at least six degrees of freedom are provided for the instrument from the base (three degrees of freedom in orientation from the instrument wrist and three degrees of freedom in position from the manipulator). More or less degrees of freedom are also within the scope of the present invention. Descriptions of F/T sensor 300 and methods of use are provided in greater detail below.

In one example, the image of the internal surgical site is shown to operator O by a stereoscopic display 12 in surgeon's console 3. The internal surgical site is simultaneously shown to assistant A by an assistance display 14.

Some of the manipulators may include a telescopic insertion axis (e.g., telescopic insertion axis 60 of FIGS. 10, 11A-14B), although in other embodiments, all of the manipulators may include a telescopic insertion axis. Telescopic insertion axis 60 allows for movement of a mounted instrument (e.g., instrument 5 or 100), via three operably coupled links, in one example, with improved stiffness and strength compared to previous designs, a larger range of motion, and improved dynamic performance and visibility proximate the surgical field for system users (in addition to other advantages), as is described in greater detail below.

For convenience, a manipulator such as manipulator 8 that is supporting a surgical tool used to manipulate tissues is sometimes referred to as a patient-side manipulator (PSM), while a manipulator 10 which controls an image capture or data acquisition device such as endoscope 11 may be referred to as an endoscope-camera manipulator (ECM). The manipulators may optionally actuate, maneuver and control a wide variety of instruments or tools, image capture devices, and the like which are useful for surgery.

Instruments 5 or 100 and endoscope 11 may be manually positioned when setting up for a surgical procedure, when reconfiguring the manipulator system 6 for a different phase of a surgical procedure, when removing and replacing an instrument with an alternate instrument 5', and the like. During such manual reconfiguring of the manipulator assembly by assistant A, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 8 (e.g., a clutch button/switch 68 in FIGS. 11A-14B), or some other component to the manipulator assembly, thereby allowing assistant A to change the manipulator mode.

As can be seen in FIGS. 1A-1C, indicators 20 may be disposed on a manipulator assembly. In this embodiment, indicators 20 are disposed on manipulators 8 near the instrument mechanical interface between the manipulators and their mounted tools 5. In alternative embodiments, clutch button/switch 68 and indicators 20 may instead be disposed on setup joints 7, 9, on tools 5, elsewhere on manipulators 8, 10, or the like. An example of an indicator is disclosed in U.S. application Ser. No. 11/556,484, filed Nov. 3, 2006, the full disclosure of which (including all references incorporated by reference therein) is incorporated by reference herein for all purposes.

Referring now to FIGS. 2-9 in conjunction with FIGS. 1A-1C, an apparatus, system, and method for sensing and feedback of forces and/or torques to the surgeon will be described with respect to using surgical instruments including strain gauges. It is noted that the below-described instruments are examples and various instruments that provide force and/or torque signals may be used in conjunction with a manipulator of the present invention.

Figure 2:
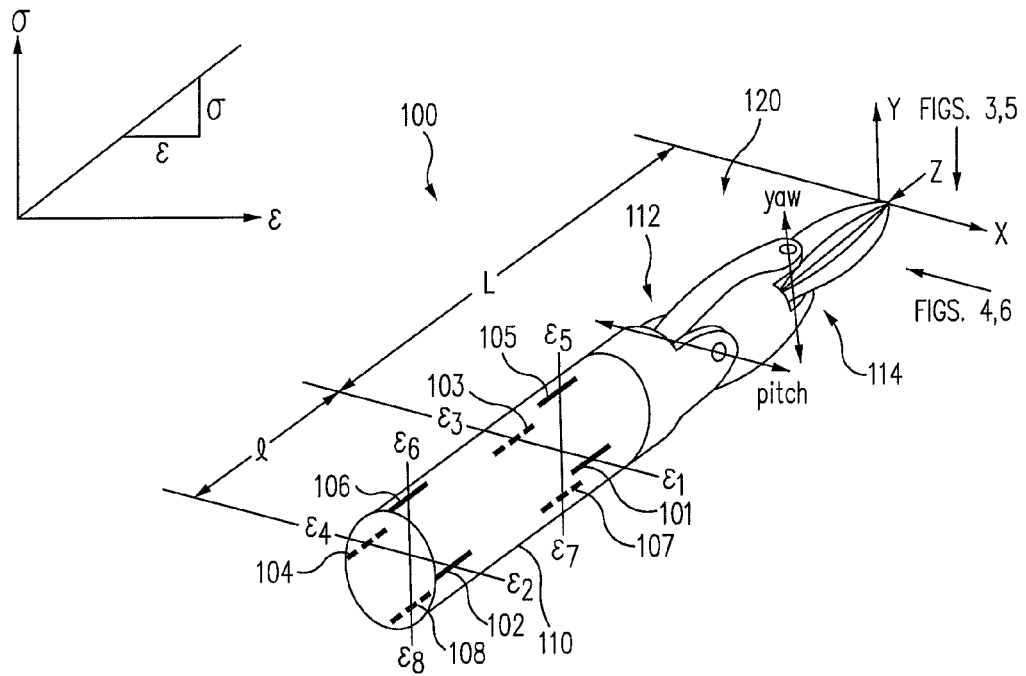
FIG. 2 is a perspective view of a surgical instrument distal end showing a wrist, grip jaws, and force sensors for use with a telerobotic surgical system in accordance with an embodiment of the present invention.

FIG. 2 shows a perspective view of a portion of a surgical instrument 100 that includes a shaft 110, wrist joints 112 and 114, and an end portion 120 that may be used to manipulate a surgical tool and/or contact the patient. The surgical instrument also includes a housing 150 (FIG. 9) that operably interfaces with a robotic manipulator arm, in one embodiment via a sterile adaptor interface. Applicable housings, sterile adaptor interfaces, and manipulator arms are disclosed in U.S. patent application Ser. No. 11/314,040 filed on Dec. 20, 2005, and U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 120 has a range of motion that includes pitch and yaw motion about the x- and y-axes and rotation about the z-axis (as shown in FIG. 2). These motions, as well as actuation of an end effector, are done via cables running through shaft 110 and housing 150 that transfer motion from the manipulator 8. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be used including but not limited to tools with and without end effectors, such as jaws, scissors, graspers, needle holders, micro-dissectors, staple appliers, tackers, suction irrigation tools, clip appliers, cutting blades, irrigators, catheters, and suction orifices. Alternatively, the surgical instrument may comprise an electrosurgical probe for ablating, resecting, cutting or coagulating tissue. Such surgical instruments are manufactured by Intuitive Surgical, Inc. of Sunnyvale, Calif.

In one example, instrument portion 100 includes sensors (e.g., strain gauges) mounted onto the exterior surface of shaft 110, oriented parallel to the longitudinal (lengthwise) axis of the shaft, termed the z-axis. The two axes perpendicular to the shaft are called the x- and y-axes. The signals from the sensors are combined arithmetically in various sums and differences (as will be explained in further detail below) to obtain measures of three perpendicular forces (e.g., $F_x$, $F_y$, and $F_z$) exerted upon the instrument tip and the torques (Tx, Ty) about the two axes perpendicular to the shaft axis (i.e., the x- and y-axes). In one example, the measurement of the forces is made independent of the orientation and effective lever arm length of a wrist mechanism at the distal end of the instrument. Forces exerted against end portion 120 are detected by the force sensing elements, which may be operably coupled to servo control via an interrogator or a processor for transmitting these forces to master(s). Examples of instruments including strain gauges and methods of force sensing are disclosed in U.S. patent application Ser. No. 11/537,241 filed on Sep. 29, 2006, and U.S. application Ser. No. 11/553,303 filed on Oct. 26, 2006, the full disclosures of which are incorporated by reference herein for all purposes.

In one embodiment, eight strain gauges 101, 102, 103, 104, 105, 106, 107, and 108 may be mounted to the outer surface of shaft 110 or in shallow recesses near the outer surface and provide strain data $\epsilon_1$, $\epsilon_2$, $\epsilon_3$, $\epsilon_4$, $\epsilon_5$, $\epsilon_6$, $\epsilon_7$, and $\epsilon_8$, respectively. The primary strain sensing direction of the gauges are oriented parallel to the z-axis. The gauges are mounted in two groups of four, wherein the four gauges in one group are spaced equally, 90 degrees apart around the circumference of the shaft at one axial position (i.e., forming two "rings" of four strain gauges each). One group of four (e.g., gauges 101, 103, 105, and 107) is mounted proximal to a wrist mechanism as close to a distal end of shaft 110 as possible. The second group of four (e.g., gauges 102, 104, 106, and 108) is mounted at a chosen distance "1" from the first group of four (toward a proximal end of shaft 110) and aligned with them so that pairs of gauges in the two groups are aligned with each other (i.e., gauges 101 and 102, 103 and 104, 105 and 106, and 107 and 108 are aligned).

The z-axis force ($F_z$) including both surgical forces and wrist cable forces is found from the sum of the eight gauge outputs multiplied by a factor of EA/8, where E is the shaft material modulus of elasticity in the z-axis direction, and A is the cross-sectional area of the shaft. The lateral forces along the x- and y-axes ($F_x$ and $F_y$) at or near the tip are found from the difference of the gauge outputs of a pair of gauges on opposite sides of the shaft and the difference between the pair differences along the shaft multiplied by a factor of EI/2rl, where E is the shaft material modulus of elasticity in the z-axis direction, I is the shaft section moment of inertia, r is the radius from the shaft axis to the acting plane of the gauges, and l is the distance between the 2 groups of 4 gauges The calculations of the forces are derived from the following equations.

With respect to FIG. 2, $E = \sigma/\epsilon$ $A = \pi(r_o^2 - r_i^2)$ $I = (\pi/4)(r_o^4 - r_i^4)$ $\sigma = (F/A) + (Mr/I)$ $\epsilon = [\epsilon_1 \epsilon_2 \epsilon_3 \epsilon_4 \epsilon_5 \epsilon_6 \epsilon_7 \epsilon_8]$ $$\begin{bmatrix} F_x \\ 1 \\ -1 \\ -1 \\ 1 \\ 0 \\ 0 \\ 0 \\ 0 \end{bmatrix} EI/2lr \quad \begin{bmatrix} F_y \\ 0 \\ 0 \\ 0 \\ 0 \\ 1 \\ -1 \\ -1 \\ 1 \end{bmatrix} EI/2lr \quad \begin{bmatrix} F_z \\ 1 \\ 1 \\ 1 \\ 1 \\ 1 \\ 1 \\ 1 \\ 1 \end{bmatrix} - EA/8$$

Figure 3:
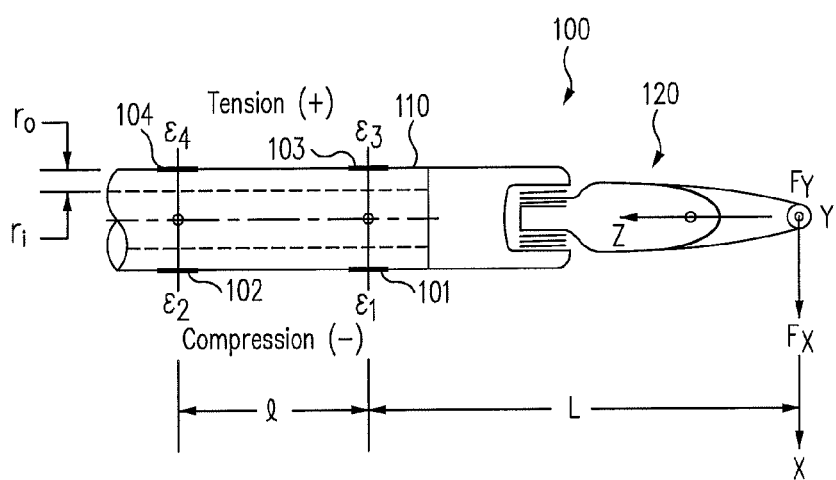
FIG. 3 is a first top view of the surgical instrument of FIG. 2 showing applied forces.
Figure 4:
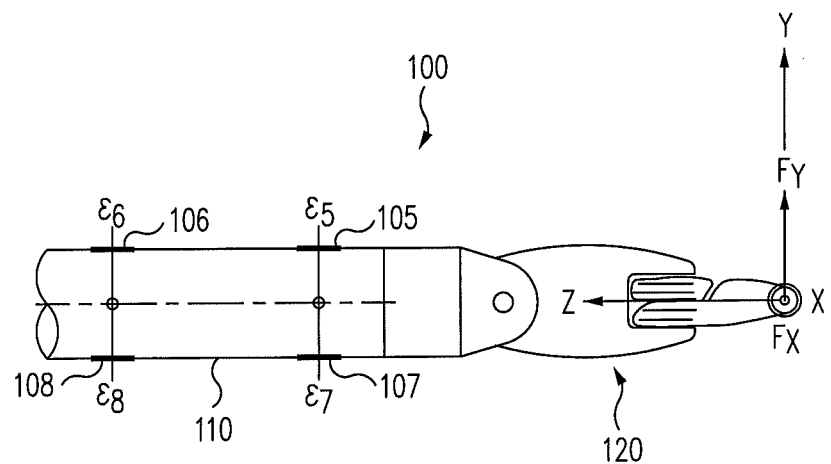
FIG. 4 is a first side view of the surgical instrument of FIG. 2 showing applied forces.

With respect to FIGS. 3 and 4, $A = \pi(r_o^2 - r_i^2)$ $I = (\pi/4)(r_o^4 - r_i^4)$ $\sigma = Mr/I$ $\sigma_1 = FLr/I$ $\sigma_2 = F(L+l)r/I$ $E = \sigma/\epsilon => \epsilon = \sigma/E$ $\epsilon_1 = -F_x Lr/EI$ $\epsilon_2 = -F_x(L+l)r/EI$ $\epsilon_2 - \epsilon_1 = -F_x lr/EI$ $\epsilon_4 - \epsilon_3 = F_x lr/EI$ $(\epsilon_4 - \epsilon_3) - (\epsilon_2 - \epsilon_1) = 2F_x lr/EI$ Thus, $(\epsilon_1 - \epsilon_2 - \epsilon_3 + \epsilon_4)EI/2lr = F_x$ $(\epsilon_5 - \epsilon_6 - \epsilon_7 + \epsilon_8)EI/2lr = F_y$ $(\epsilon_1 + \epsilon_2 + \epsilon_3 + \epsilon_4 + \epsilon_5 + \epsilon_6 + \epsilon_7 + \epsilon_8)EA/8 = F_z$ $F_x$ and $F_y$ are thus invariant with respect to L and invariant with respect to temperature at steady state.

Advantageously, instrument 100 allows for making the measured transverse forces (Fx, Fy) at the instrument tip independent of variations in the effective lever arm length due to wrist orientation changes or gripping position changes in the end portion during surgery. The measured transverse forces are also made independent of changes in the z-axis forces especially those due to the varying wrist cable tensions. Further, the measured transverse forces are independent of both surgical and wrist friction induced torques applied distal to the combined groups of strain gauges. Finally, the measured forces along the x- and y-axes are independent of temperature changes when at thermal equilibrium over all gauges. This may be seen by adding an equal temperature disturbance strain to all four gauges in the equations for $F_x$ and $F_y$ and noting that the disturbances cancel. Thermal transients during which gauge temperatures are unequal are not compensated by this design although other measures may be taken to do so.

The measurements of the torques about the x- and y-axes (Tx and Ty) at the instrument tip are derived from the differences of the gauges paired across the shaft diameter and the sum of the pair differences along the shaft axis multiplied by a factor EI/4r, wherein once again E is the shaft material modulus of elasticity in the axial direction, I is the shaft section moment of inertia, and r is the radius from the shaft axis to the acting plane of the gauges. Thus the forces (Fx, Fy, Fz) and torques (Tx, Ty) exerted at the instrument tip are measured without errors due to wrist orientation or the location of a gripped tool such as a suture needle within jaws or tissue held in a grasper, for example. Torque measurements about the x- and y-axes are also independent of temperature at steady state. The calculations of the torques are derived from the following equations.

Figure 5:
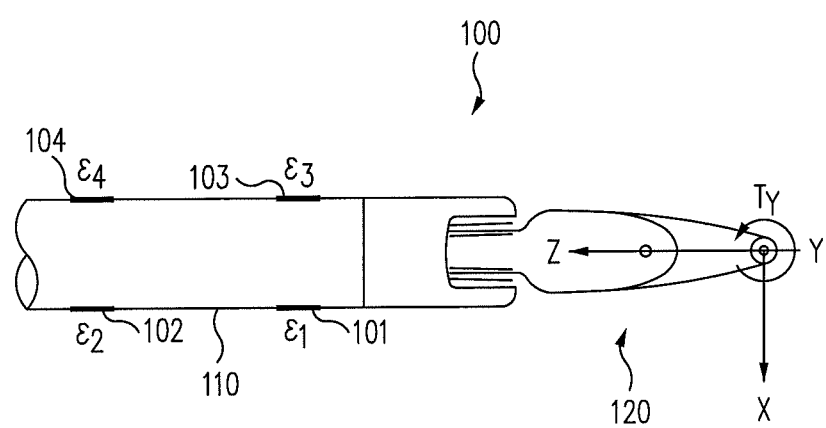
FIG. 5 is a second top view of the surgical instrument of FIG. 2 showing applied torque.
Figure 6:
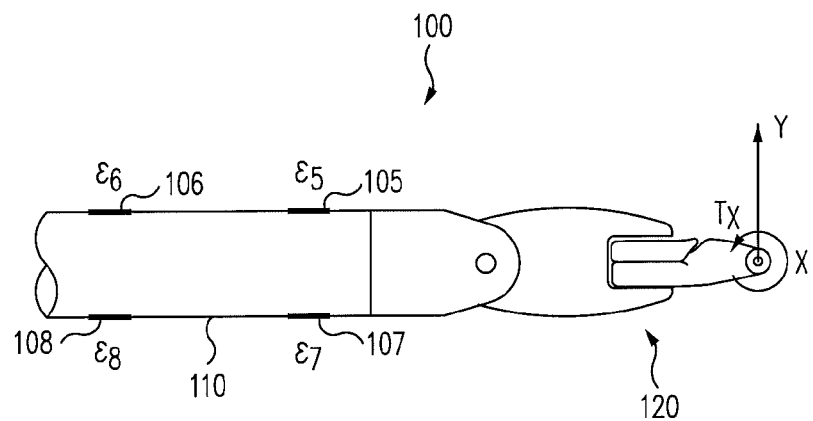
FIG. 6 is a second side view of the surgical instrument of FIG. 2 showing applied torque.

With respect to FIGS. 5 and 6 in conjunction with FIG. 2, $$\begin{bmatrix} T_x \\ 0 \\ 0 \\ 0 \\ 0 \\ -1 \\ -1 \\ 1 \\ 1 \end{bmatrix} EI/4r \quad \begin{bmatrix} T_y \\ 1 \\ 1 \\ -1 \\ -1 \\ 0 \\ 0 \\ 0 \\ 0 \end{bmatrix} EI/4r$$

$\sigma = Mr/I$ $\sigma_1 = \sigma_2 = Tr/I$ $E = \sigma/\epsilon => \epsilon = \sigma/E$ $\epsilon_1 = \epsilon_2 = Tr/EI$ Thus, $(\epsilon_1 + \epsilon_2 - \epsilon_3 - \epsilon_4)EI/4r = T_y$ $(-\epsilon_5 - \epsilon_6 + \epsilon_7 + \epsilon_8)EI/4r = T_x$ Although a variety of constructions are possible, instrument 100 is preferably constructed with anisotropic linear fiber reinforced polymer tubing, in one example, because all gauges are oriented parallel to the z-axis with constant and easily characterized elastic properties. Similar advantages may be gained with properly characterized woven reinforced tubing, and the method is also applicable to uniform elastic property tubing.

In one example, various strain gauges may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft.

As an example, with no intention to limit the invention thereby, two commercially available fiber strain gauge technologies may be used. A Fabry-Perot technology is commercially available from FISO Technologies, Inc. of Quebec, Canada, with more information available at http://www.fiso.com. A fiber Bragg grating (FBG) gauge technology is commercially available from Smart Fibres Ltd. of Bracknell, England, with more information available at http://www.smartfibres.com.

Multiple FBGs can be written into a fiber if they are formed in such a way as to use a different range of wavelengths, and as noted above, this is a particularly useful property for the double ring of strain gauges embodiment because only four fibers would need to be embedded into the instrument shaft, each with two FBGs separated by a known distance. To implement the double ring arrangement of strain gauges with the Fabry-Perot technology, eight fibers would be required.

Both fiber technologies require an interrogator unit that decodes the optically encoded strain information into electrical signals compatible with the computer control hardware of the robotic surgical system. A processor may then be used to calculate forces according to the equations outlined above in conjunction with the signals from the strain gauges/sensors. In one embodiment, an interrogator unit 170 (FIG. 9) is mounted on the manipulator, or elsewhere in the surgical system, which may require routing of the optical fiber across the sterile boundary. In one case, an optical coupling is incorporated into the standard instrument mechanical interface with the manipulator such that installation of an instrument onto the manipulator automatically forms an optical link with the instrument. Advantageously, this avoids the need to carry external cabling to the instrument. In a second case, a fiber pigtail exits the top of the instrument for mating with a connector presented on the manipulator but not part of the instrument mechanical interface. In these two cases, the interrogator may be built into the manipulator or fiber cables may run through the manipulator to an interrogator mounted on the surgical system or in the operating room separate from the manipulator. In a third case, a fiber pigtail exits the top of the instrument without passing through the manipulator for mating with an interrogator unit mounted in the operating room separate from the manipulator, which has the benefit of not requiring connection of the fiber cable when the instrument is attached or removed from the manipulator.

Other combinations of gauge orientations, numbers of gauges, and outputs are also possible. A useful simplification of the two ring eight gauge arrangement is to remove one of the rings of gauges. This simplification removes the ability to distinguish between forces and moments on a given axis (e.g., x or y), but many items in the surgical environment (e.g., human tissue, sutures) do not support moments well, and thus it is possible to assume that all strain information is from x- and y-axis forces. In a further embodiment, three gauges 120 degrees apart may be used to form a set instead of four gauges 90 degrees apart. Thus, combinations of gauges may include a single ring of three gauges 120 degrees apart, two rings of three gauges each 120 degrees apart (i.e., a total of six gauges), a single ring of four gauges 90 degrees apart, and two rings of four gauges each 90 degrees apart (i.e., a total of eight gauges). Single ring gauge embodiments may be useful for non-wristed tools such as probes. Gauges may also be oriented on the surface of shaft 110 at angles that permit recovery of the additional torque signal $T_z$ about the shaft axis. However, the off-axis elastic properties of the shaft must be taken into account.

X- and y-axis forces may be detected with sensor(s) at the distal end of the instrument shaft as disclosed above, and z-axis forces may be detected with a sensor(s) located outside of the body near the proximal end of the instrument. Various sensors may be used outside of the body for detecting z-axis forces, including but not limited to strain gauges and/or fiber technologies.

Typically, z-axis forces cannot be easily sensed at the instrument tip because the instrument shaft is subject to significant internal forces in the z-direction from the internal cabling necessary for transmitting torques to the instrument pitch and yaw axes. These cables run inside the instrument shaft, and experiments have shown that the compression loads on the shaft vary significantly as the instrument is operated. Attempts to sense z-direction strain with gauges on the instrument shaft will include a significant cable actuation "noise" in addition to the applied z-axis force of interest. Thus, it is preferred that z-axis forces be sensed in a location substantially not subject to internal cabling forces. It is noted that these cables also impart some x- and y-moments at the base of the shaft because the cables are not completely centered and because cable tension on either side of the wrist pulleys will vary as the wrist is operated. However, experiments have shown that, unlike the z-direction cable forces, these variations are relatively small compared to the expected externally applied forces.

Z-axis forces may be detected outside the body with relative accuracy with mainly the cannula seal friction and sliding friction of the shaft in the cannula adding "noise" to the signal of interest. In one embodiment, cannula seals are disposable and may be packaged with friction reducing lubrication or a friction reducing coating (such as Parylene) which is bonded to the cannula seal surfaces. In another embodiment, the instrument shaft surfaces may be treated with a friction reducing coating (e.g., PTFE) to reduce undesirable friction noise. Both friction reducing methods may also be used simultaneously.

In one example, a sensor may be placed in various locations outside of the body proximate the proximal end of the surgical instrument. It is preferred that the sensor be built into the manipulator rather than the disposable instrument, but this is not necessary. In one embodiment, a sensor(s) 160 (FIG. 9) may be positioned at mount points for the instrument sterile adaptor on the manipulator arm insertion (z-axis) carriage (e.g., on a carriage link which is described in greater detail below). In another embodiment, a sensor(s) may be placed at the instrument backplate. This would be substantially equivalent to placing sensors on the sterile adaptor mount points but would require an additional sensor be built into every instrument.

By contrast to the z-axis forces, the x- and y-axis forces cannot easily be sensed outside the body because of contact with the cannula which in turn is subject to the large patient body wall forces and torques imparted at the remote center that mask the comparatively small x- and y-axis tissue contact forces. Thus, it is preferred that x- and y-axis forces be sensed in a location substantially not subject to body wall forces or torques such as the distal end of the instrument shaft proximal to the instrument wrist joint as discussed above. In the disclosure above, a force-torque sensor integrated with the tubular distal end of an endoscopic surgical instrument shaft is described. In one embodiment, the sensor comprises two sets of four strain gauges located about the periphery of the shaft such that the members of a group of four are 90 degrees apart around the shaft and the two groups of four are a distance 1 apart along the shaft. In one aspect, it was desired to determine the side load (e.g., $F_y$) on the instrument tip or jaws. The disclosure explains that by computing the bending moment at each group of sensors due to the side load and then subtracting the two values, a measure of the side load independent of wrist orientation and resulting effective lever arm length can be derived. A concern is that the moments applied to the distal end of the shaft by the actuation of the instrument wrist axes and transmitted to the shaft by the friction in the wrist pivots will interfere with the intended measurement of the side loads. However, by carrying the terms due to such moments through the arithmetic governing the measured strains, it may be seen that the terms due to such moments drop out when the side load forces are calculated. Similarly, the z-axis forces drop out.

Figure 7:
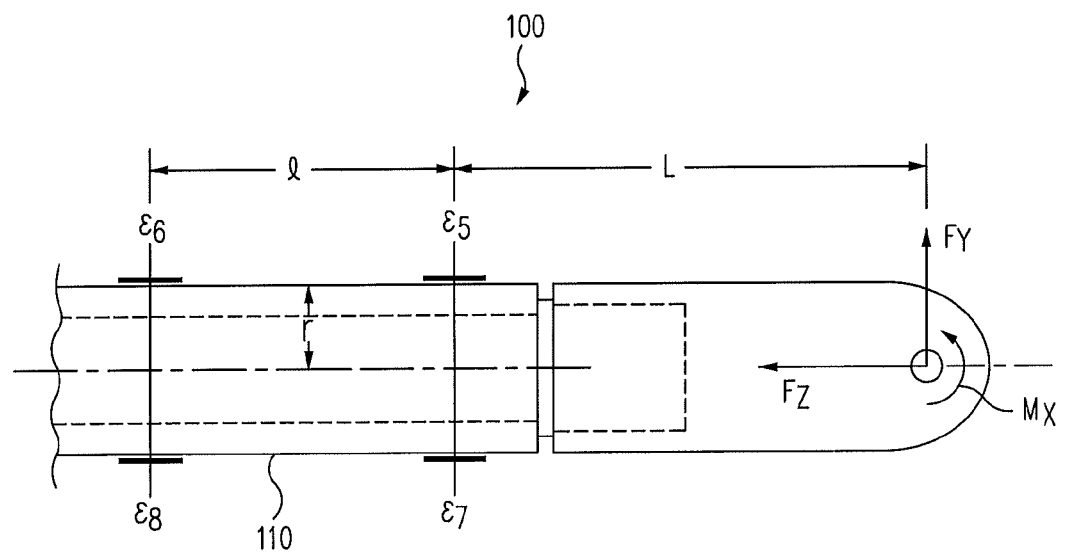
FIG. 7 shows a free body diagram of the instrument shaft and proximal wrist clevis subjected to loads and moments applied by the wrist mechanism.

Referring now to FIG. 7 and the equations below, by proper arithmetic combination of the strains sensed by the eight strain gauges, it is possible to eliminate the unwanted axial wrist cable forces and wrist actuation torques while preserving the desired side load forces. FIG. 7 illustrates a free body diagram of the shaft subjected to loads and moments applied by the wrist mechanism. A variety of forces and moments may apply to the free body of the outboard wrist 120 (FIG. 6). Depending on the combination of tip loads, cable loads, and motion and acceleration of the wrist, the forces and moment applied to the end of the shaft 110 viewed in the y-z plane of the shaft reduce to $F_y$ (side load), $F_z$ (axial load), and $M_x$ (wrist pivot friction moment load).

Therefore, one can express the strains $\epsilon_5$, $\epsilon_6$, $\epsilon_7$, and $\epsilon_8$ on the four gauges in this plane in terms of these three loads and derive the expression for the desired side force $F_y$ as follows:

Tensile strain>0
Compressive strain<0

$$\varepsilon_7 = -F_z/EA + M_x r/EI + F_y Lr/EI$$

$$\varepsilon_5 = -F_z/EA - M_x r/EI - F_y Lr/EI$$

$$\varepsilon_8 = -F_z/EA + M_x r/EI + F_y(1+L)r/EI$$

$$\varepsilon_6 = -F_z/EA - M_x r/EI - F_y(1+L)r/EI$$

$$[(\varepsilon 8 - \varepsilon 6) - (\varepsilon 7 - \varepsilon 5)] = -F_z/EA[(1-1)-(1-1)] +$$
$$M_x r/EI[(1-(-1))-(1-(-1))] +$$
$$F_y r/EI \left\{ \begin{array}{c} [(1+L)-(-(1+L))] - \\ [L-(-L)] \end{array} \right\}$$
$$= 2lF_y r/EI$$

Therefore, $$F_y = [(\epsilon_8-\epsilon_6)-(\epsilon_7-\epsilon_5)]EI/2lr$$

$M_x$ and $F_z$ do not appear.

As can be seen, the strains due to the moment load $M_x$ which are felt identically on both sets of gauges drop out, leaving the moment loads due to the applied side force $F_y$. The strain components due to the axial force $F_z$, also felt identically on both sets of gauges, also drop out. Therefore, since the wrist actuating torques are transmitted to the shaft carrying the strain sensors by the friction in the wrist joint, they result in moment loads that cancel when the signals from the two sets of sensors are subtracted, leaving a relatively clean signal due to the side force load alone as desired. The above disclosure similarly applies to $\epsilon_{1-4}$ in the x-z plane with x and y interchanged.

Calculating a clean signal due substantially to the side force load alone advantageously eliminates the need to place the sensor outboard of (distal to) the wrist joints as previously done to eliminate the wrist friction moments. The present invention thus avoids the need to route wires or optic fibers associated with the strain gauges through the flexing wrist joint. Furthermore, the yaw and grip axes may be accomplished on the same pivot axis rather than having them separate as previously done.

For all of the methods and apparatus mentioned above, it may be advantageous to use a calibration process in which forces and torques are applied to the instrument tip serially, simultaneously, or in combinations while correction factors and offsets are determined to apply to the theoretical equations described above for combining the gauge outputs to obtain $F_x$, $F_y$, $F_z$, $T_x$, and $T_y$. Calibration may be accomplished either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Figure 8:
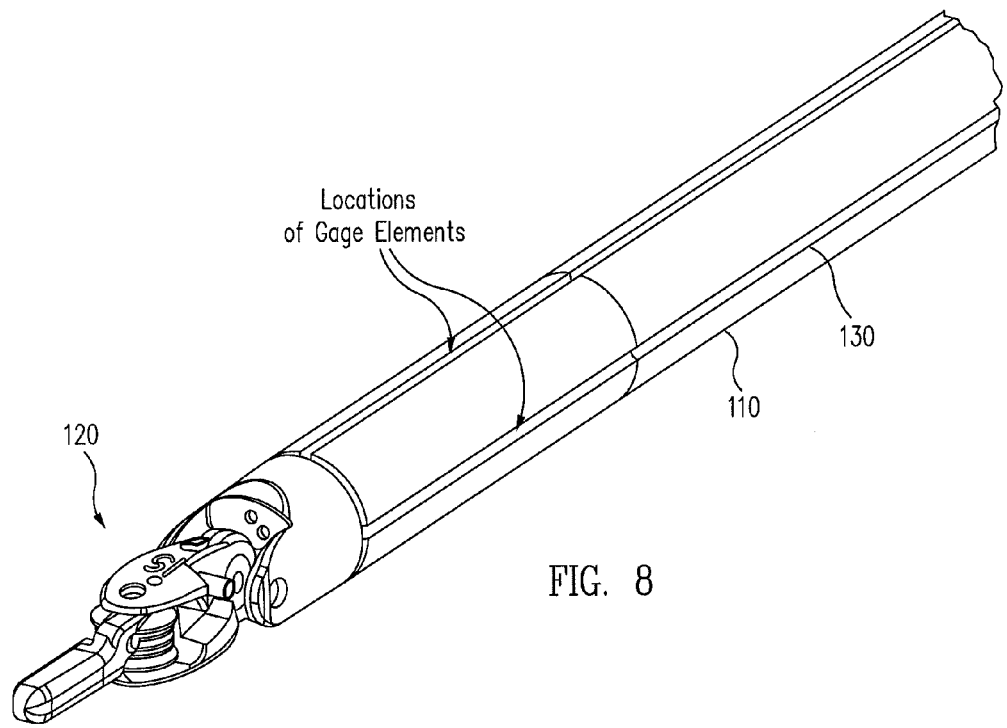
FIG. 8 shows a grooved instrument shaft for embedded strain gauges.
Figure 9:
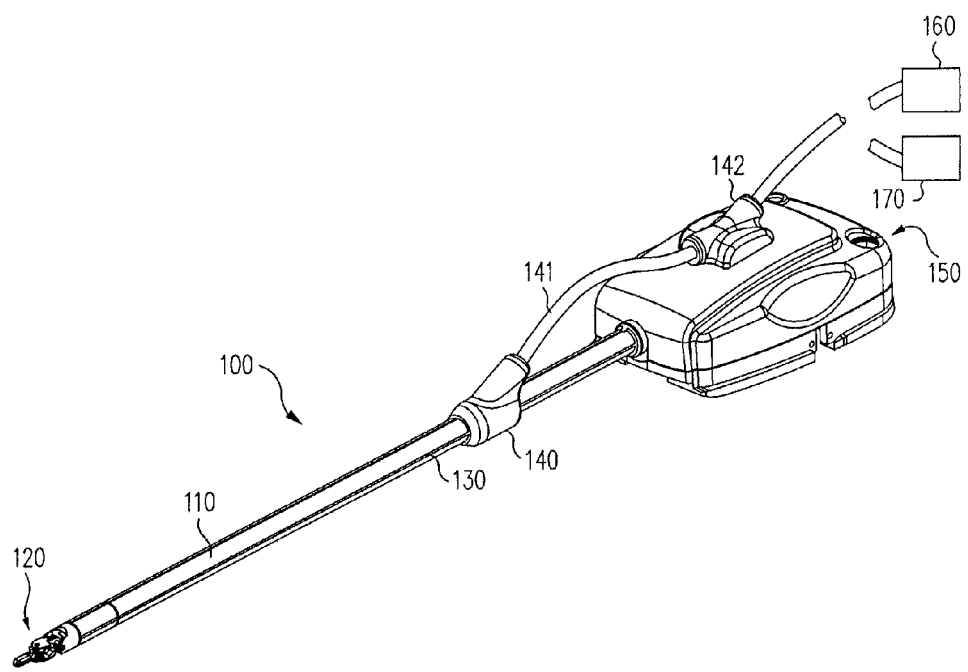
FIG. 9 shows an instrument including strain gauges.

Optical fibers embedded in the instrument shaft preferably should exit the shaft near the proximal end of the instrument in a way that does not impede rotation of the shaft relative to the instrument housing/carriage while preserving the physical integrity of the fiber. Referring now to FIGS. 8 and 9, Fabry-Perot or FBG sensing elements may be embedded in shallow grooves 130 just below the shaft 110 surface near the instrument shaft distal tip just behind the wrist clevis, and then epoxied or otherwise potted into place. Grooves 130 may lead back toward the proximal end of the instrument, which includes the motion inputs and wrist cable actuator mechanism (the "housing") 150. Grooves 130 may be formed in the shaft during the initial pultrusion process, or the grooves may be machined after shaft production. At a point near the proximal mechanism or housing, the fibers may be routed out of the grooves at a gentle angle and bundled through a strain relief 140 into a protective flexible sheath 141 which would carry the optical fibers to a strain relieved anchor point 142 on the top cover of the mechanism housing 150. The flexible sheath 141, strain relief 140, and anchor point 142 should have sufficient length and flexibility to permit safe repeated flexing and torsion as the instrument shaft 110 is rotated.

In another embodiment, if the instrument shaft is made with resin and fiber (e.g., fiberglass or carbon fiber), the optical fibers may be woven or embedded with linear axial reinforcing fibers at the desired angular (90 or 120 degrees) and radial (near surface) positions into the instrument shaft fiber matrix prior to the application of resin.

As noted above, z-axis forces may be detected outside the body with relative accuracy, with mainly the cannula seal friction and sliding friction of the shaft in the cannula adding "noise" to the signal of interest. Advantageous embodiments of a cannula, a cannula seal, an instrument, and methods of use are described for reducing friction to substantially reduce noise when determining z-axis forces in U.S. application Ser. No. 11/864,974, which has been previously incorporated by reference.

Referring to FIG. 9, a perspective view of instrument 100 is illustrated. In one embodiment, the exterior of instrument shaft 110 includes surfaces treated with a friction reducing coating (e.g., polytetrafluoroethylene (PTFE), Parylene, or polyamide) and/or is comprised of friction reducing materials to negate undesirable friction noise. Shaft 110 may be of a uniform diameter covering strain gauges positioned in grooves along the instrument shaft as described above such that the entire shaft of the instrument may pass through a cannula and/or a cannula seal with minimal friction or snagging.

Figure 10:
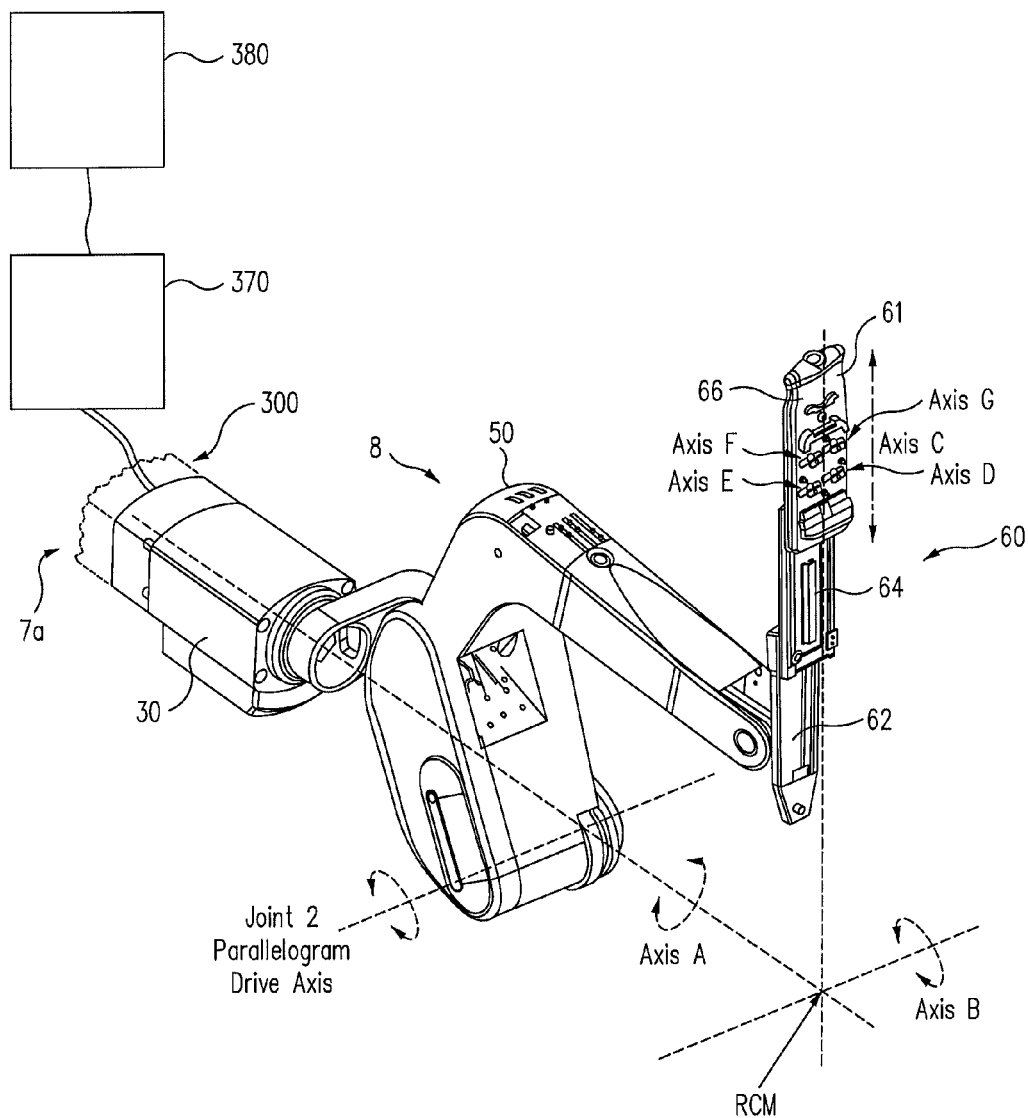
FIG. 10 is a perspective view of a manipulator, including a force sensor at a base of the manipulator, in accordance with an embodiment of the present invention.
Figures 11A, 11B:
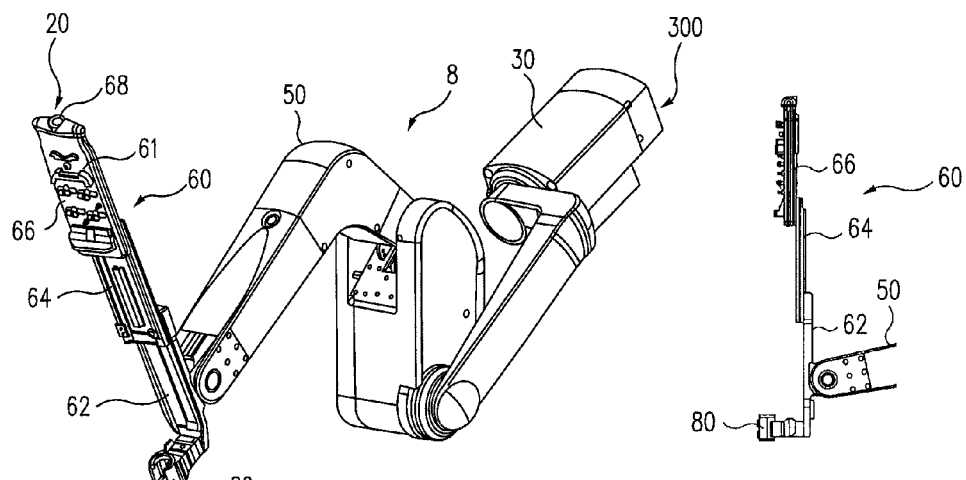
FIGS. 11A and 11B are a perspective view and respective side view of the manipulator of FIG. 10, including the coupling of an accessory clamp, in accordance with an embodiment of the present invention.
Figures 12A, 12B:
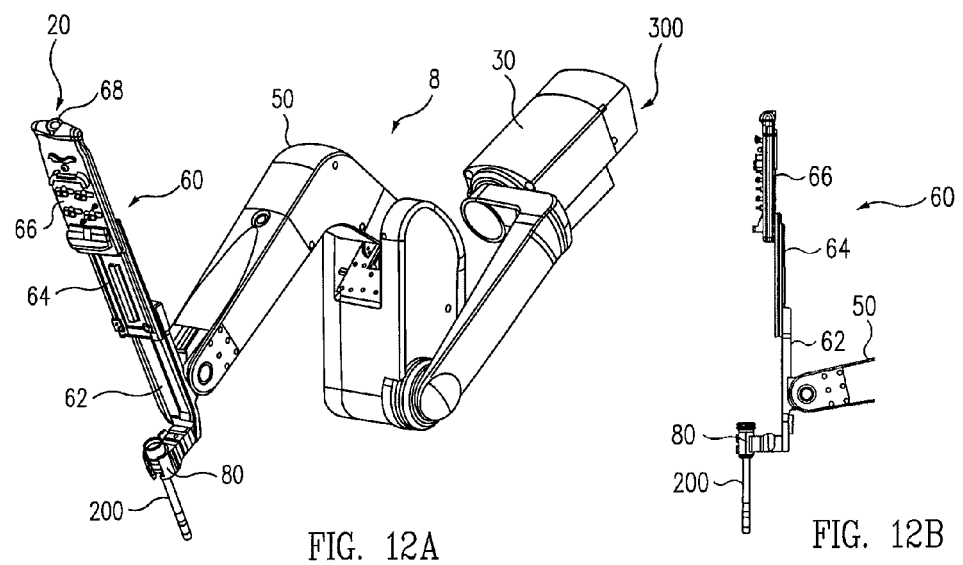
FIGS. 12A and 12B are a perspective view and respective side view of the manipulator of FIG. 10, including the coupling of a cannula, in accordance with an embodiment of the present invention.
Figures 13A, 13B:
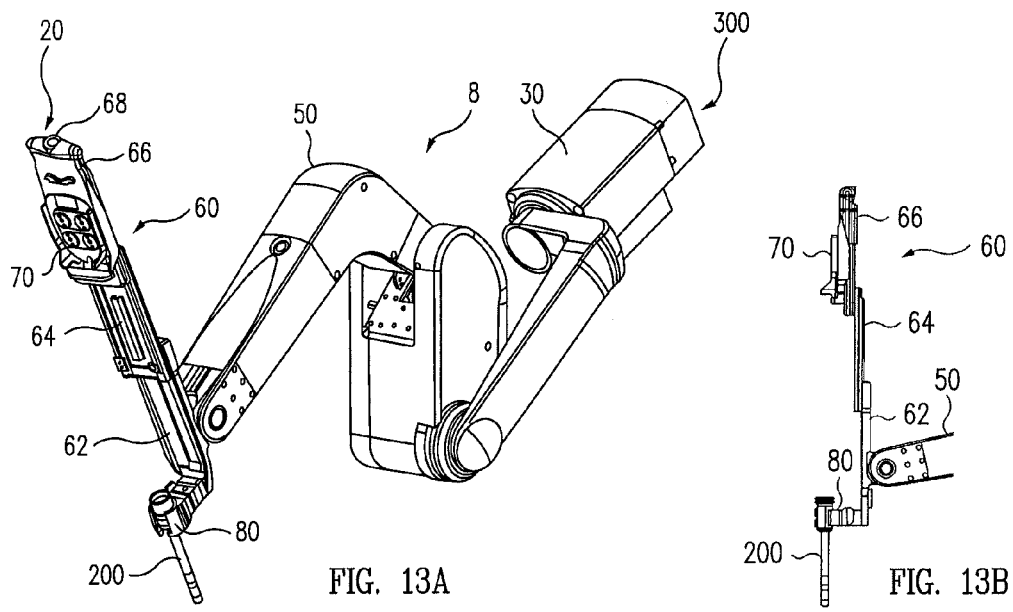
FIGS. 13A and 13B are a perspective view and respective side view of the manipulator of FIG. 10, including the coupling of a sterile adaptor, in accordance with an embodiment of the present invention.
Figures 14A, 14B:
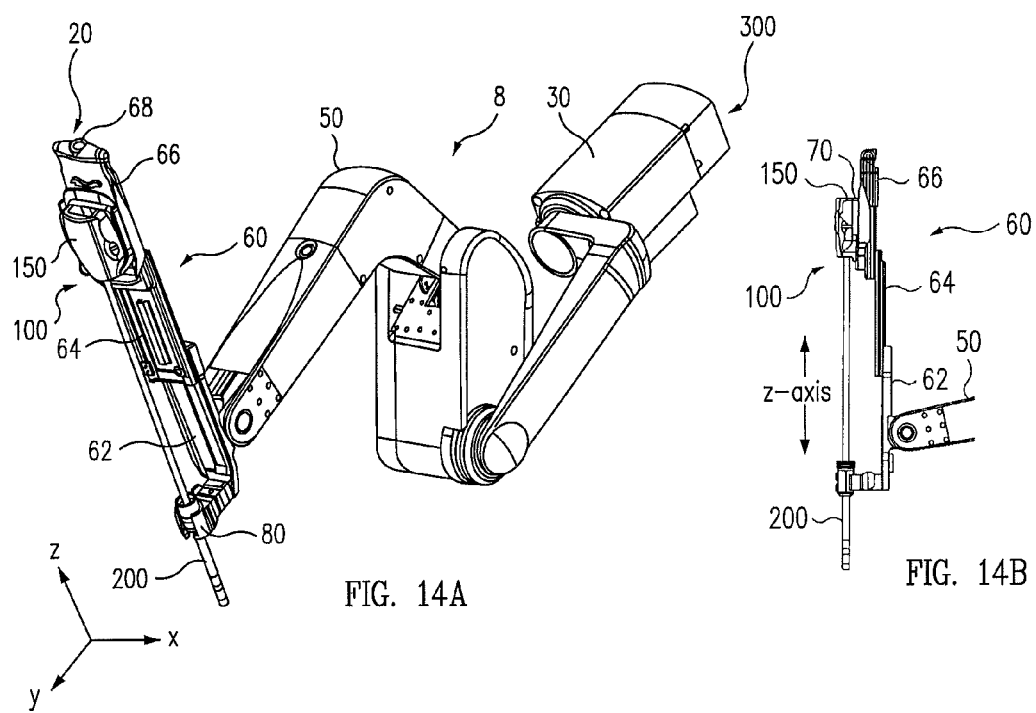
FIGS. 14A and 14B are a perspective view and respective side view of the manipulator of FIG. 10, including the coupling of an instrument, in accordance with an embodiment of the present invention.

Referring now to FIGS. 10-14B, perspective views and respective side views of a manipulator 8 including a base-mounted F/T sensor 300, a manipulator arm link 50, and a telescopic insertion axis 60 are shown in accordance with an embodiment of the present invention. In FIG. 10, a F/T sensor interface 370 is operably coupled to F/T sensor 300, and a computer 380 is optionally coupled to F/T sensor interface 370. FIGS. 11A-11B illustrate the coupling of an accessory clamp 80, FIGS. 12A-12B illustrate the coupling of a cannula 200, FIGS. 13A-13B illustrate the coupling of an instrument sterile adaptor 70, and FIGS. 14A-14B illustrate the coupling of an instrument 100.

In one embodiment, telescopic insertion axis 60 includes a first link or base link 62, a second link or idler link 64 operably coupled to base link 62, and a third link or carriage link 66 operably coupled to idler link 64. Some of the manipulators include a telescopic insertion axis 60, although in other embodiments, the manipulators may include a linear sliding carriage or a telescopic insertion axis 60. In yet other embodiments, the insertion axis 60 may include a smaller or greater number of links. Telescopic insertion axis 60 allows for movement of mounted tool or instrument 100, via three operably coupled links, with improved stiffness and strength compared to previous designs, a larger range of motion, and improved dynamic performance and visibility proximate the surgical field for system users (in addition to other advantages), as is described in greater detail in pending U.S. application Ser. No. 11/613,800, filed Dec. 20, 2006, which is incorporated by reference herein for all purposes.

Base link 62 is operably coupled to a distal end of manipulator arm link 50, and in one example has an accessory clamp 80 attached to a distal end of base link 62. A cannula 200 may be mounted onto accessory clamp 80. An example of applicable accessory clamps and accessories are disclosed in pending U.S. application Ser. No. 11/240,087, filed Sep. 30, 2005, the full disclosure of which is incorporated by reference herein for all purposes. An example of applicable sterile adaptors and instrument housings are disclosed in U.S. application Ser. No. 11/314,040, filed Dec. 20, 2005 and in U.S. application Ser. No. 11/395,418, filed Mar. 31, 2006, the full disclosures of which are incorporated by reference herein for all purposes.

Carriage link 66 includes an instrument interface for operably coupling (e.g., electrically and/or physically) to an instrument sterile adaptor (ISA) 70 (FIGS. 13A-13B), which is capable of operably coupling (e.g., electrically and/or physically) to a housing of an instrument (e.g., housing 150 of FIGS. 14A and 14B), and controls the depth of the instrument inside a patient. In one embodiment, the sterile adaptor is integrated with a drape that may be draped over the robotic surgical system, and in particular the manipulator system, to establish a sterile barrier between the non-sterile manipulator arms (e.g., a patient side manipulator as further described below) and the sterile field of the surgical procedure. An example of an applicable drape and adaptor is disclosed in pending U.S. application Ser. No. 11/240,113, filed Sep. 30, 2005, the full disclosure of which is incorporated by reference herein for all purposes. An example of an instrument interface is disclosed in pending U.S. application Ser. No. 11/613,695, filed Dec. 20, 2006, the full disclosure of which is incorporated by reference herein for all purposes.

Idler link 64 is movably coupled between base link 62 and carriage link 66 to allow the links 62, 64, and 66 to move relative to one another along a lengthwise axis in a telescoping fashion. In one embodiment, base link 62 has a narrower form factor than idler link 64, and idler link 64 has a narrower form factor than carriage link 66, thus providing for greater visibility near the surgical field.

For convenience, a manipulator such as manipulator 8 that is supporting a surgical tool used to manipulate tissues may be referred to as a patient-side manipulator (PSM), while another manipulator which controls an image capture or data acquisition device such as an endoscope may be referred to as an endoscope-camera manipulator (ECM). The manipulators may optionally actuate, maneuver and control a wide variety of instruments or tools, image capture devices, and the like which are useful for surgery.

Instruments 100 may be manually positioned when setting up for a surgical procedure, when reconfiguring the manipulator system for a different phase of a surgical procedure, when removing and replacing an instrument with an alternate instrument, and the like. During such manual reconfiguring of the manipulator assembly by an assistant, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 8 (e.g., a clutch button/switch 68 in FIGS. 11A-14A), or some other component to the manipulator assembly, thereby allowing the assistant to change the manipulator mode.

Figure 15:
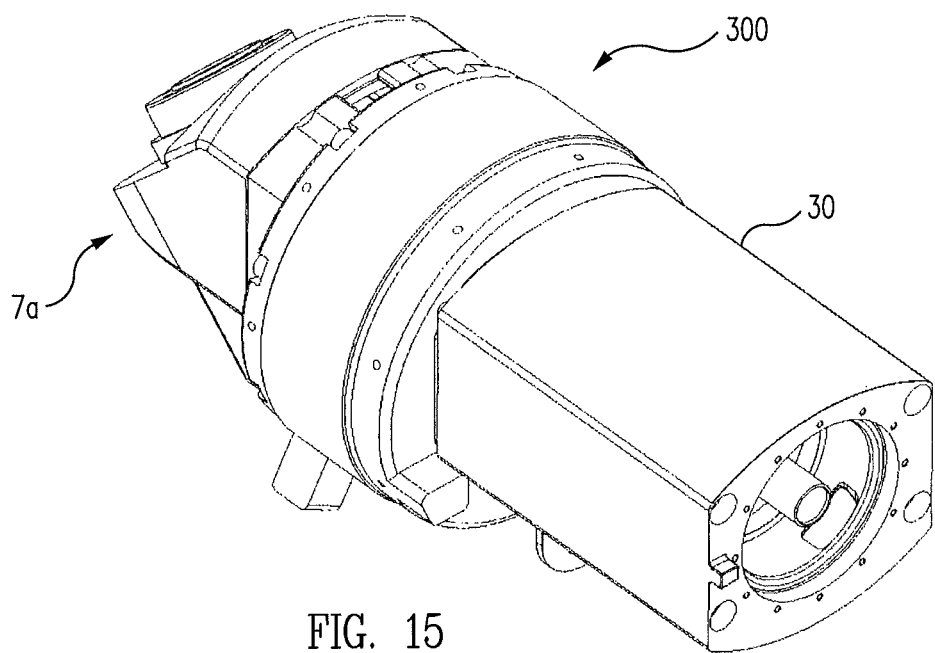
FIG. 15 illustrates a close-up perspective view of the force sensor at the base area of the manipulator.
Figure 16:
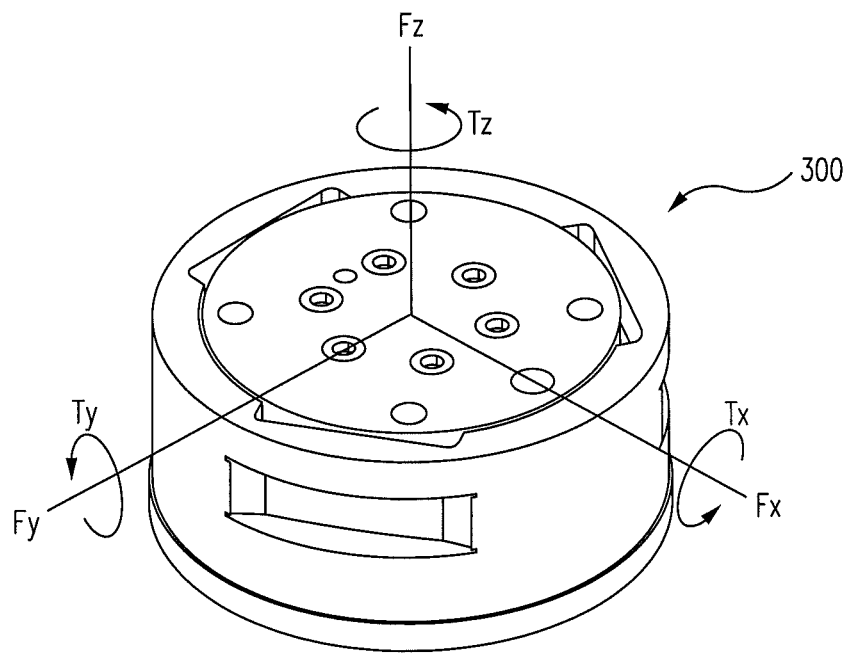
FIG. 16 illustrates an example of the force sensor in accordance with an embodiment of the present invention.

Referring now to FIGS. 15 and 16, FIG. 15 illustrates a close-up perspective view of the F/T sensor 300 between a free end 7a of a setup linkage arm 7 and a base 30 of the manipulator 8, and FIG. 16 illustrates an example of the F/T sensor 300 without mechanical or electrical connector interfaces.

As noted above, F/T sensor 300 is operably coupled between a base of a manipulator (e.g., a base 30 of manipulator 8 or 10, FIGS. 1A-1C) and outboard the respectively coupled linkage (e.g., at a free end 7a of linkage 7 or 9). In one embodiment, sensor 300 is operably coupled between base 30 and a free end 7a of a linkage (see FIGS. 1A-1C). In one example, one side of F/T sensor 300 is operably attached to the end of a passive setup arm linkage and another side of F/T sensor 300 is operably attached to a servo-actuated manipulator at base 30. In another example, at least six degrees of freedom are provided for the manipulator (and instrument) beginning at base 30. In particular, yaw, pitch, and insertion axis movement of manipulator 8 outside a patient body are provided for along axes A, B, and C (FIG. 10). Pitch and yaw movement of an instrument wrist, and roll movement of the instrument provide three other degrees of freedom beginning at (i.e. distal to) base 30. More or less degrees of freedom are also within the scope of the present invention. For example, the opening and closing of an instrument end effector may be considered another degree of freedom.

F/T sensor 300 is in one example a monolithic structure that converts force and torque into analog strain gauge signals for F/T sensor interface 370 (FIG. 10). In one example, as shown in FIG. 16, sensor 300 includes three symmetrically-placed beams that flex upon application of force to the sensor. The beams may be machined from solid metal in one example. Semiconductor strain gauges or foil resistive strain gauges are attached to the beams and may be considered strain-sensitive resistors that provide to F/T sensor interface 370 strain gauge signals related to force and torque components in the x, y, and z-axes (Fz, Tz, Fy, Ty, Fz, and Tz).

Communication between F/T sensor interface 370 and sensor 300 may be accomplished through an electrically shielded cable with operable connectors for connecting to the sensor and the interface. Various other communication means between sensor 300 and F/T sensor interface 370, including both wired and wireless communication means and protocols, are within the scope of the present invention.

F/T sensor interface 370 converts strain gauge data from F/T sensor 300 to force/torque components. The resistance of the strain gauges on sensor 300 change as a function of applied loads. F/T sensor interface 370 measures the change in resistance and converts this change to force and torque components using a combination of hardware and software and calibration data. F/T sensor interface 370 may also provide power and signals to the sensor 300 as well as reading the sensor outputs. A computer 380 (FIG. 10) may also be operably coupled to F/T sensor interface 370 for further processing of strain gauge data. F/T sensor interface 370 may communicate with computer 380 through various means, including but not limited to a serial input/output or an analog output. In one example, F/T sensor interface 370 may output raw strain gauge data and/or resolved force/torque data in various formats, including but not limited to hexadecimal and decimal integer formats.

In one example, with no intent to limit the invention thereby, F/T sensor 300 is a force/torque transducer, model Theta, available from ATI Industrial Automation, of Apex, N.C., and an example of F/T sensor interface 370 is an applicable power supply and data acquisition (DAQ) card or Controller F/T system, also available from ATI Industrial Automation, of Apex, N.C. More information is available at http://www.ati-ia.com.

Referring now to FIGS. 17A-17F, mechanical and electrical connector interfaces between a F/T sensor, a setup linkage arm, and a base of a manipulator arm are illustrated, in accordance with an embodiment of the present invention.

Figure 17A:
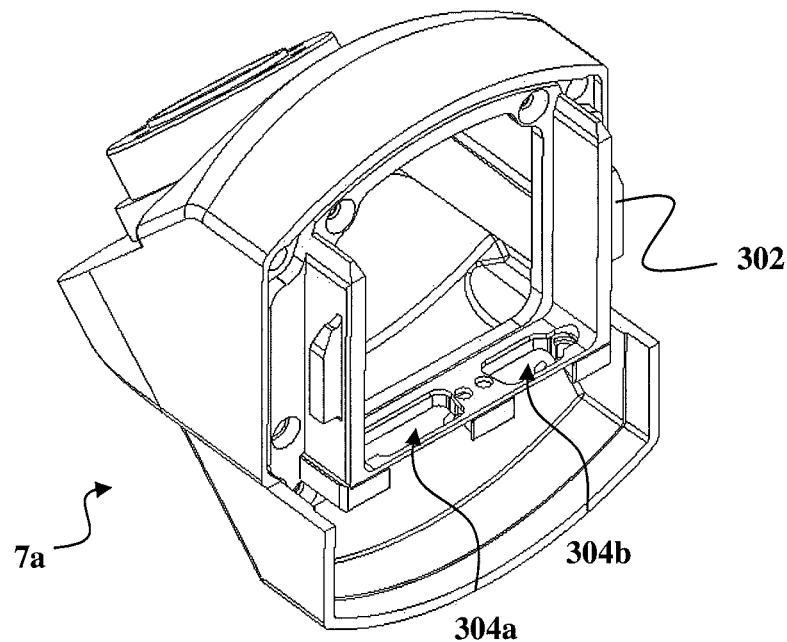
FIGS. 17A-17F illustrate mechanical and electrical connector interfaces between a F/T sensor, a setup linkage arm, and a base of a manipulator arm in accordance with embodiments of the present invention.
Figure 17B:
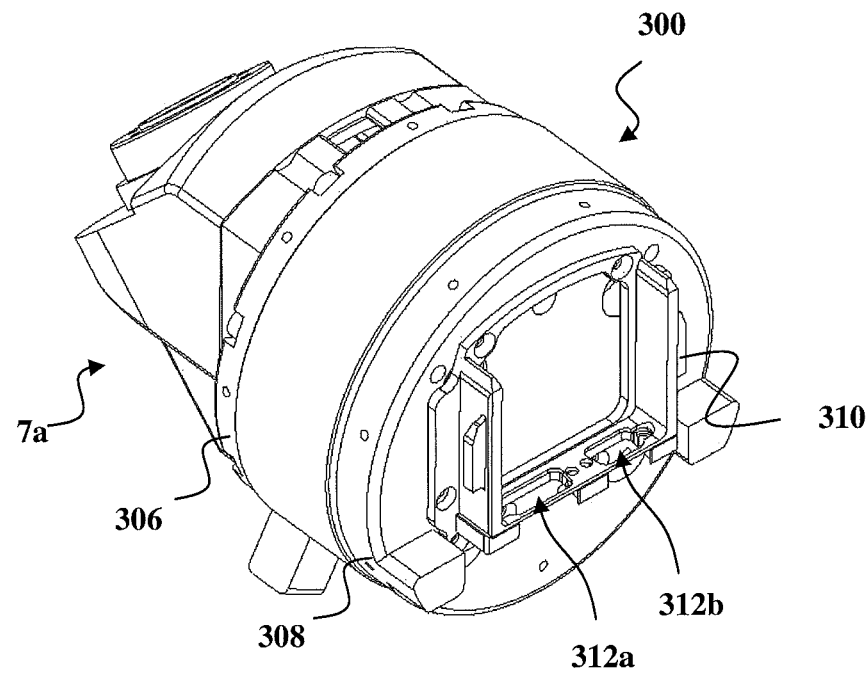
Figure 17C:
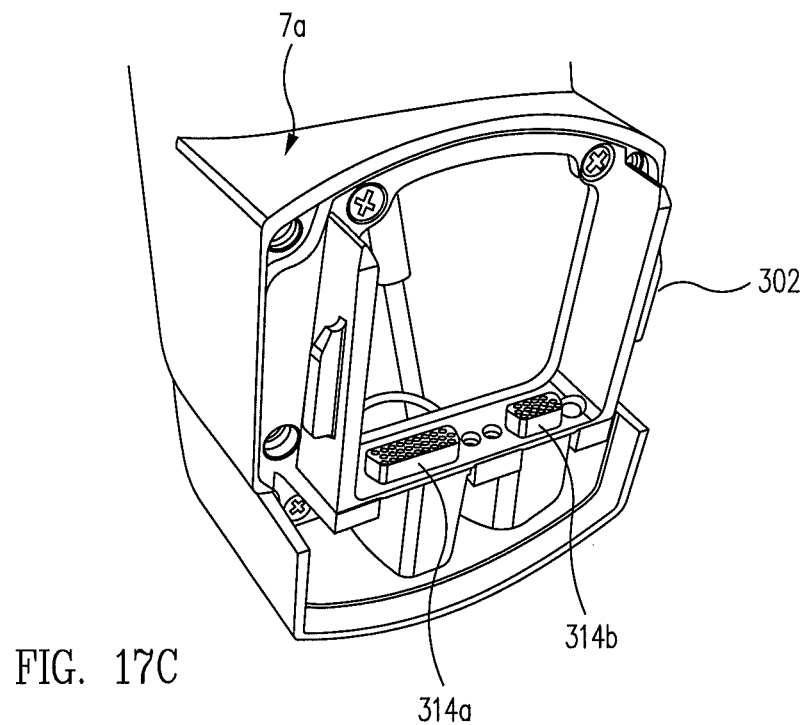
Figure 17D:
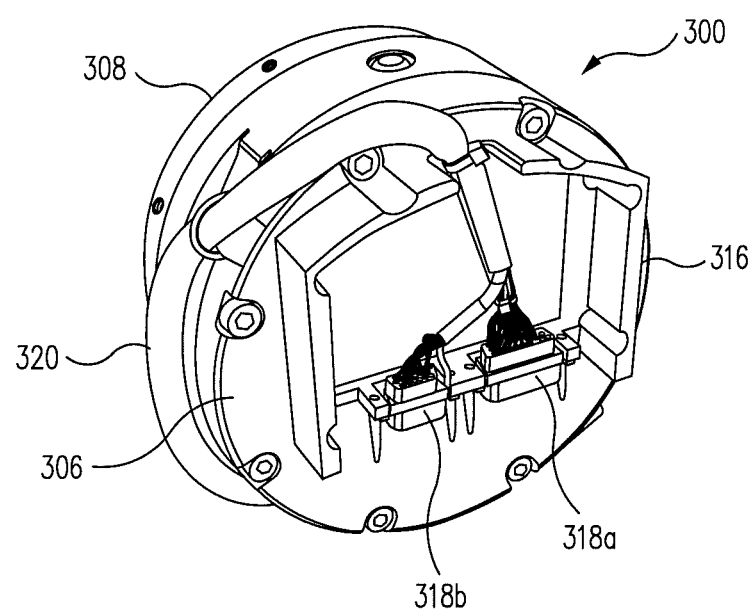
Figure 17E:
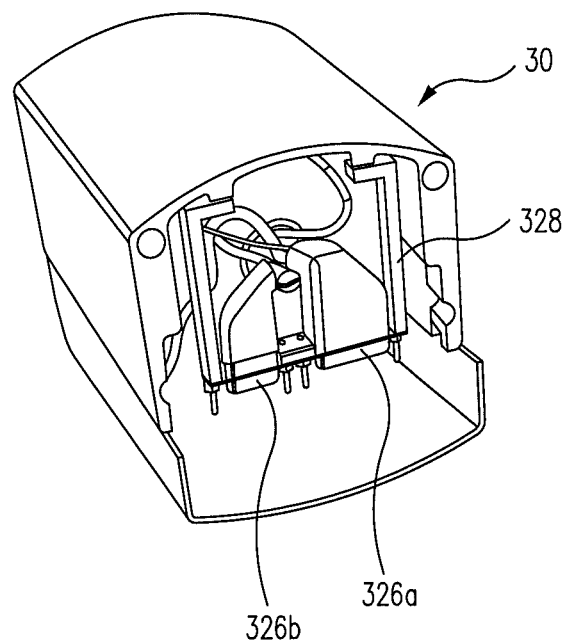
Figure 17F:
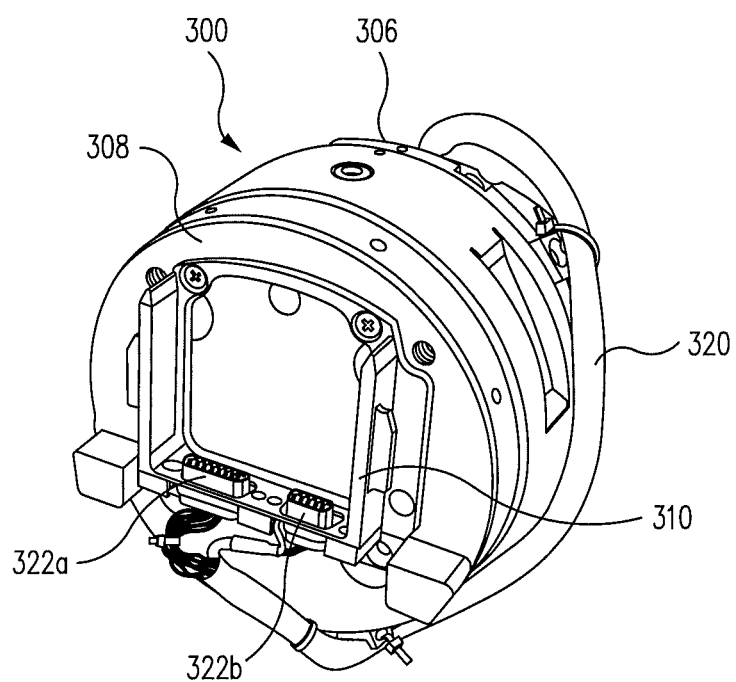

A combination of aligning slots and screws may be used for mechanical coupling of F/T sensor 300 between a setup linkage and a manipulator in one example. In one embodiment, slots 302 are provided on setup linkage free end 7a, slots 328 are provided on base 30, and the F/T sensor 300 includes on a first side a mechanical and electrical connector interface 306 that mechanically couples to free end 7a and on a second side a mechanical and electrical connector interface 308 that mechanically couples to base 30. Interface 306 includes slots 316 that slidably couple to slots 302 (FIGS. 17C and 17D) and interface 308 includes slots 310 that slidably couple to slots 328 (FIGS. 17E and 17F). The slots and screws slidably engage and secure the sensor to the set-up linkage and the base of the manipulator in one example.

In another example, a combination of D-type connectors (plugs and sockets) and wires may be used for electrical coupling of F/T sensor 300 between a setup linkage and a manipulator for passing of power and data. In one embodiment, setup linkage free end 7a includes sockets 314a, 314b that fit in openings 304a, 304b and interface 306 of F/T sensor 300 includes plugs 318a, 318b that operably couple to sockets 314a, 314b (FIGS. 17C and 17D). In another embodiment, base 30 includes plugs 326a, 326b and interface 308 of F/T sensor 300 includes sockets 322a, 322b that operably couple to plugs 326a, 326b (FIGS. 17E and 17F). Power and data are passed from a first side to a second side of the F/T sensor by coupling plugs 318a, 318b to sockets 322a, 322b via sheathed wires 320 which are routed around an exterior surface of F/T sensor 300 in one embodiment. In other embodiments, sheathed wires 320 may be routed through the F/T sensor 300.

Figure 18:
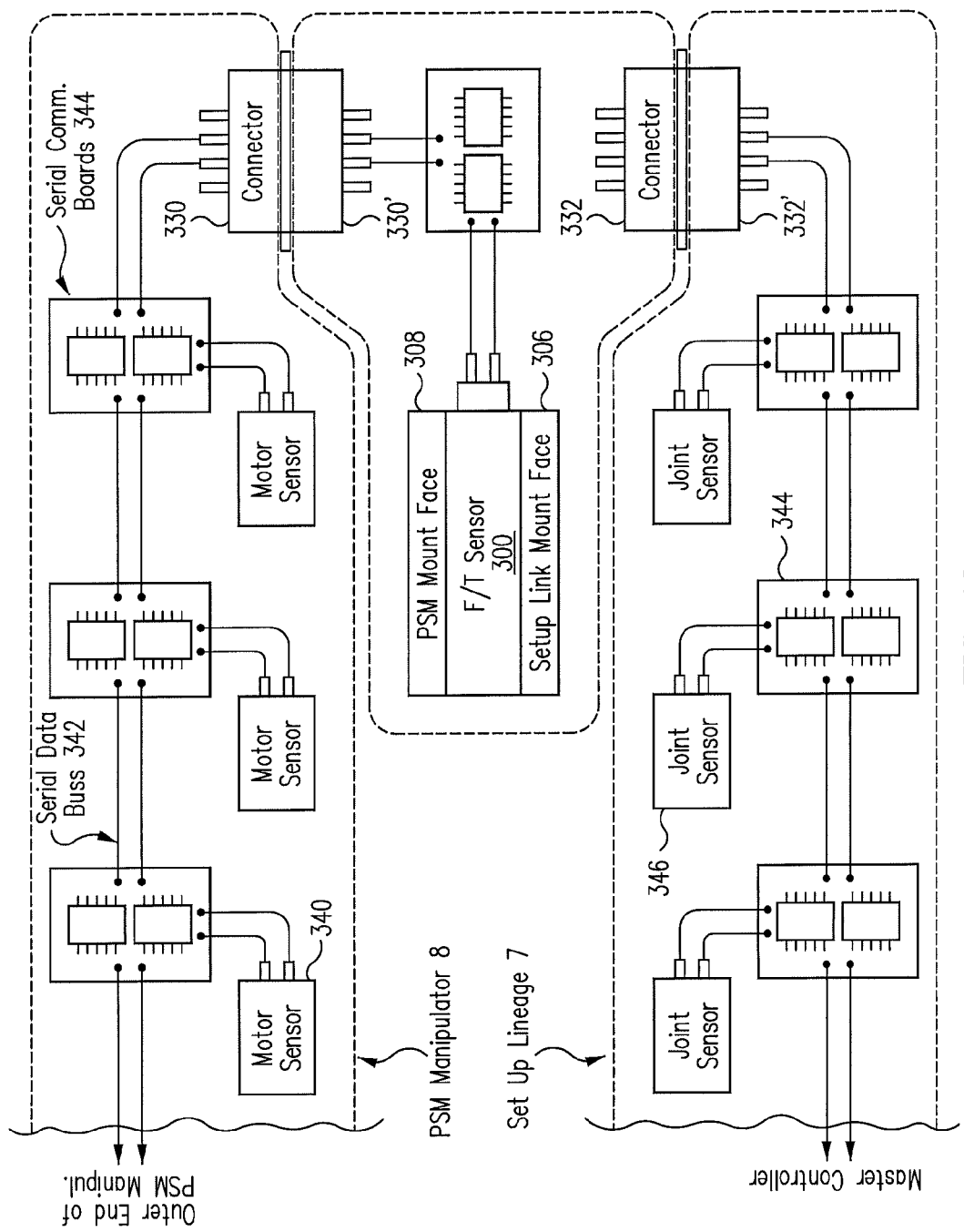
FIG. 18 illustrates a block diagram of the data coupling between the F/T sensor, a setup linkage arm, and a manipulator arm in accordance with an embodiment of the present invention.

Referring now to FIG. 18, a block diagram of a data signal pathway between the F/T sensor 300, the setup linkage arm 7, and the manipulator arm 8 is illustrated in accordance with an embodiment of the present invention. In one embodiment, F/T sensor signals are injected into an additional node (e.g., a serial communication board 344) on a serial bus 342 that passes from motor sensors 340 in a manipulator arm 8, through a setup linkage 7 including joint sensors 346, and to a main controller. Connectors 330, 330' and 332, 332' allow for electrical connection between F/T sensor 300 and the manipulator 8 and setup linkage 7, respectively. In one example, connectors 330, 330' and 332, 332' may be similar to the D-type connectors described above with respect to FIGS. 17A-17F. Advantageously, the use of serial communication allows for time division multiplexing of F/T sensor signals with the sensor signals from manipulator motor sensors 340 and set-up linkage joint sensors 346.

Other mechanical and electrical engagement means between the sensor and the base or the linkage are within the scope of the present invention. The plugs and sockets described above may be serial and/or parallel connectors and male and female connectors may be applicably switched. Other types of electrical interfaces such as Ethernet, Universal Serial Bus, and FireWire are also within the scope of the present invention. Advantageously, the mechanical and electrical engagement means described above allow for efficient and simple mechanical and electrical mating between the F/T sensor and the setup linkage or the manipulator base.

Figure 19A:
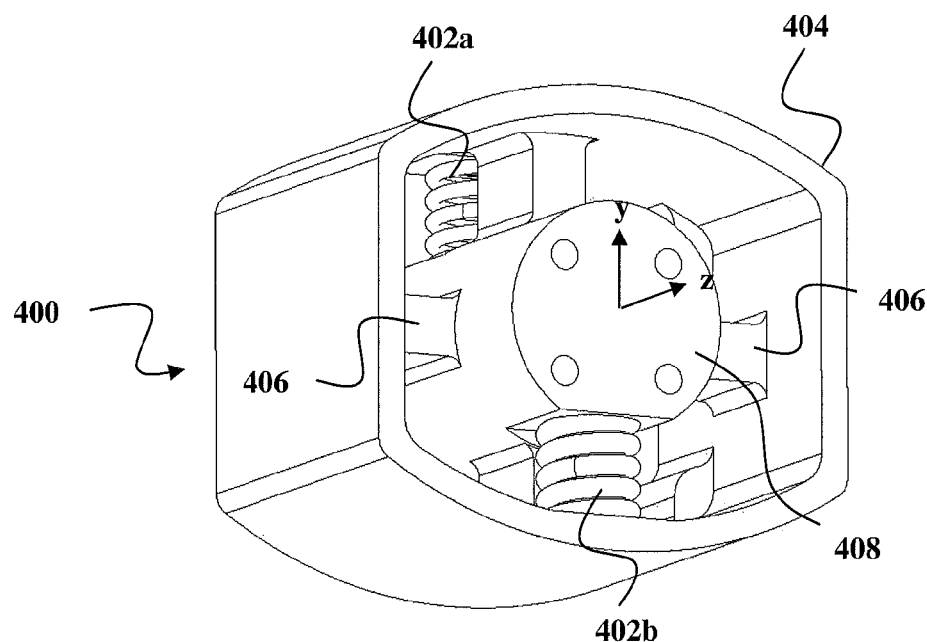
FIGS. 19A and 19B illustrate a spring counterbalance in a F/T sensor in accordance with an embodiment of the present invention.
Figure 19B:
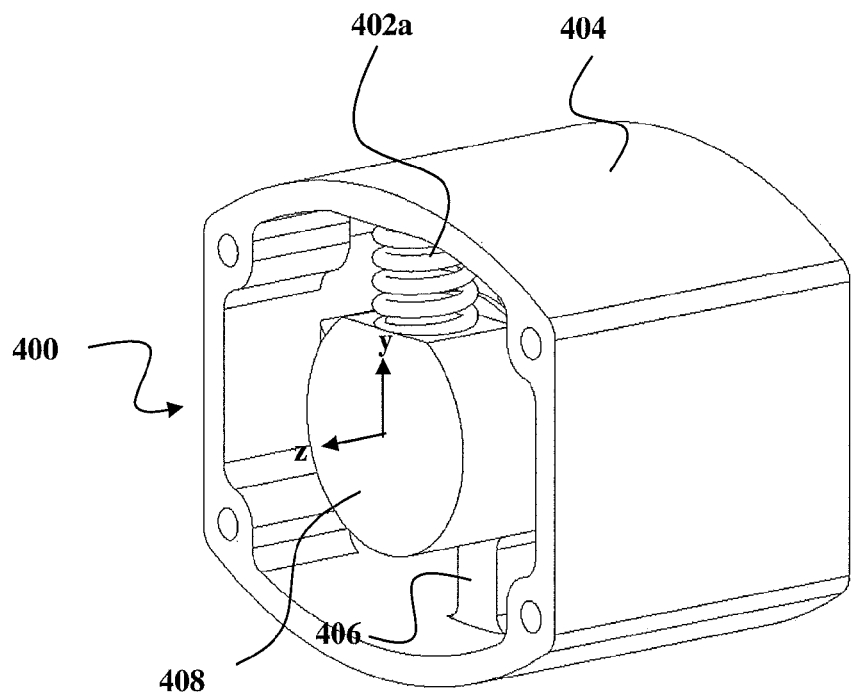

Referring now to FIGS. 19A and 19B, a spring counterbalance for a F/T sensor 400 is illustrated in accordance with an embodiment of the present invention. F/T sensor 400 comprises a housing 404 with four struts 406 about a central hub 408 of the sensor in one example. In this embodiment, hub 408 is operably coupled to a manipulator and housing 404 is operably coupled to a setup linkage. Strain gauges are mounted on the struts 406. Springs 402a and 402b are positioned at opposite ends of the sensor along a lengthwise axis "z" and also above and below center hub 408 along a vertical axis "y". The force of spring 402b is greater than the force of spring 402a by an amount equal to a weight of the manipulator mounted to center hub 408. Advantageously, the position of springs 402a and 402b counteracts an overhanging load weight and moment of the manipulator. Other means of applying load compensating force and moment to the hub carrying the manipulator are possible such as flexure beams and the like and are within the scope of the present invention. Such counterbalanced F/T sensor designs permit a smaller, lighter sensor with smaller struts than would otherwise be required to support the manipulator while operating within safe stress limits. The signal to noise ratio of the strain gauges is also improved because the gauges can operate over a larger fraction of their dynamic range centered around zero strain rather than centered around a strain corresponding to the uncompensated static overhanging load of the manipulator. In either case the maximum strain permitted by the gauges or the strut stress is substantially the same. Finally, the role of the sensor hub and outer housing may be reversed with respect to mounting to the setup link and the manipulator if the spring positions are changed accordingly (e.g., by flipping the sensor over).

In operation, insertion axis 60 has an instrument 100 mounted to it passing through a cannula 200 in an incision and then into the patient (FIGS. 14A-14B). Manipulator 8 is therefore connected to mechanical ground through (1) the F/T sensor 300 to the passive setup linkage (e.g., linkage 7) to the setup cart; and also through (2) the cannula to incision to patient body wall to the operating table. Both ground paths have mechanical compliance, and therefore both paths carry a share of robot and instrument loads to mechanical ground. Thus, forces applied to the instrument tip may pass to mechanical ground partly through the patient body wall rather than the base mounted F/T sensor.

Because of the combined setup arm and patient body wall compliance, there are vibration modes of the combined base mounted F/T sensor and robot mass on the end of the setup arm. Different methods may be used to remove "noise" from the sensor signals. A notch filter may be used on the strain gauge data to remove forces due to the vibration of the force sensor and robot mass. A low pass filter may be used to remove higher frequency noise on the strain signals leaving only the lower frequency surgical forces. Patient body wall forces caused by tilting of the cannula in the incision may also be removed by mapping these forces as a function of cannula tilt angles and subtracting the resulting estimated body wall forces from the total sensed forces, using a look-up table in one instance. A minimum-sensing threshold may also be used to eliminate forces at or below a F/T sensor noise floor level.

A base mounted F/T sensor may be used in conjunction with instruments including or not including strain gauges. Accordingly, the base mounted F/T sensor and instrument strain gauges may be used together to provide a robust sensing system, including x-, y-, and z-axis force sensing, although in other embodiments the base mounted F/T sensor may be used alone. In one example, the base mounted F/T sensor may be used to augment the instrument tip force sensor by sensing forces applied proximal to the instrument tip force sensor including collisions of the instrument shafts with each other and collisions of the robot arms outside the body. In a second example, the base mounted F/T sensor may be used to augment the instrument tip force sensor by combining the resolved instrument z-axis (stem tube axis) forces measured by the base mounted F/T sensor with the instrument x- and y-axis (transverse axes) forces measured by the instrument tip sensor.

F/T sensor interface 370 or computer 380 may filter the strain gauge data from the base mounted F/T sensor using a low-pass filter(s), a notch filter(s), a low signal level deadband, and combinations thereof to reduce sensor noise.

In one example, a low-pass filter may be used to filter the force/torque data to detect incipient suture breaking and rise in forces leading to the breaking, and collisions between surgical instruments inside a patient body.

In another example, a notch filter tuned to the resonance of the manipulator and F/T sensor mass compliantly constrained by the setup linkage arm and patient body wall may be used in combination with a low pass filter to reduce sensor noise and a variable gain circuit dependent on the inverse of the instrument tip or robotic arm velocity to attenuate the force signal when it is dominated by dynamic forces due to movement of the robotic arm. This filtering scheme may be used to detect, for example, incipient suture breaking, collisions between surgical instruments inside a patient body, tissue dissection, retraction, and palpation.

In another example, the signals from the F/T sensor may be filtered by magnitude to distinguish between forces on the manipulator arm internal and external to a patient body. Thus, collisions of the manipulator arm external to the patient body and internal surgical forces on the manipulator arm may be distinguished based upon a magnitude of a signal from the F/T sensor.

The force/torque sensor information may then be displayed to a surgeon with a visual, auditory, or haptic feedback.

Figure 20:
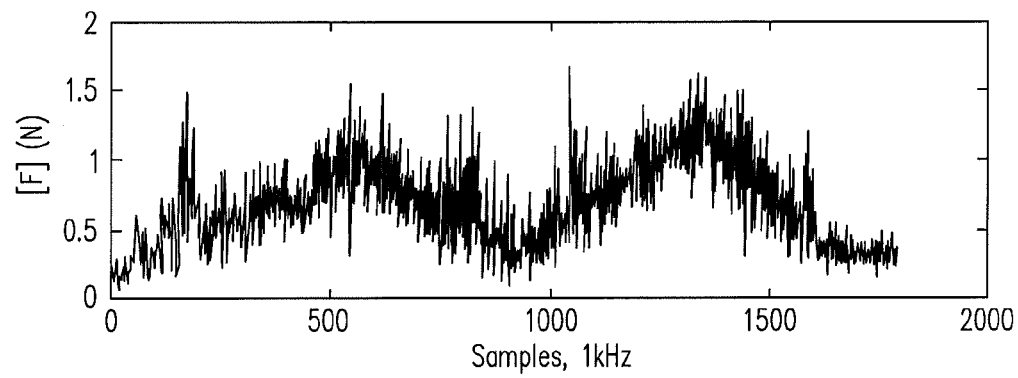
FIG. 20 illustrates a maximum variation in force readings from a manipulator of the present invention including a base-mounted force sensor during a particular test.

Referring now to FIGS. 20-25, different experimental force readings are shown from a manipulator of the present invention including a base-mounted F/T sensor. A tool was installed on a PSM including a base-mounted sensor, and the tool was moved into position over an approximately 3 inch cut in simulated (rubber) tissue. The F/T sensor output reading was set to zero, thereby negating static gravity loads. The operator at the surgeon's console moved the tip of the instrument along the length of the cut to establish the expected static variation of the signal over this workspace. The maximum variation in this particular test was approximately 1.7 N as illustrated in FIG. 20.

Figure 21:
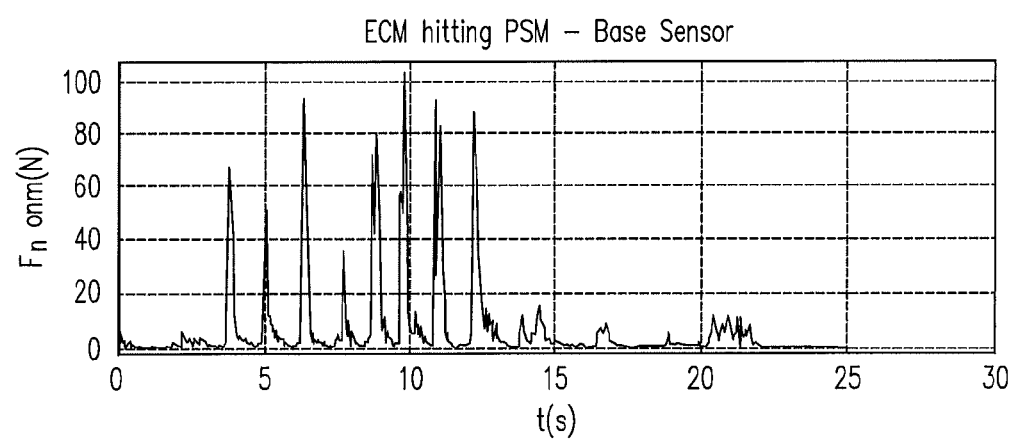
FIG. 21 illustrates force readings from the manipulator of the present invention including a base-mounted force sensor when another manipulator hits the manipulator of the present invention external to the patient.

FIG. 21 illustrates force readings from a manipulator (e.g., PSM) of the present invention when another manipulator (e.g., ECM) hits the manipulator of the present invention external to the patient. Peak disturbances from approximately 40 N to 100 N sensed by the manipulator are clearly provided.

Figure 22:
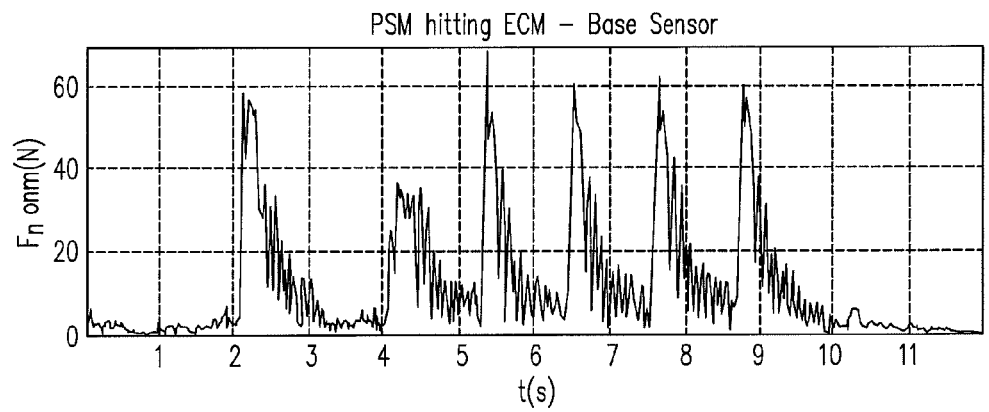
FIG. 22 illustrates force readings from the manipulator of the present invention including a base-mounted force sensor when the manipulator of the present invention hits another manipulator external to the patient.

FIG. 22 illustrates force readings from the manipulator (e.g., PSM) of the present invention when the manipulator of the present invention hits another manipulator (e.g., ECM) external to the patient. Peak disturbances from approximately 30 N to 60 N sensed by the manipulator are clearly provided.

Figure 23:
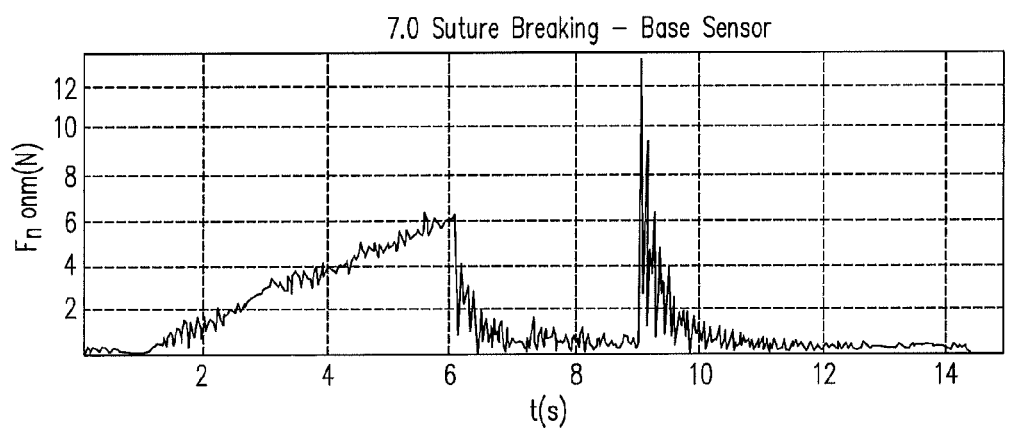
FIG. 23 illustrates force readings from the manipulator of the present invention including a base-mounted force sensor when the manipulator of the present invention progressively increases force and finally breaks a suture.
Figure 24:
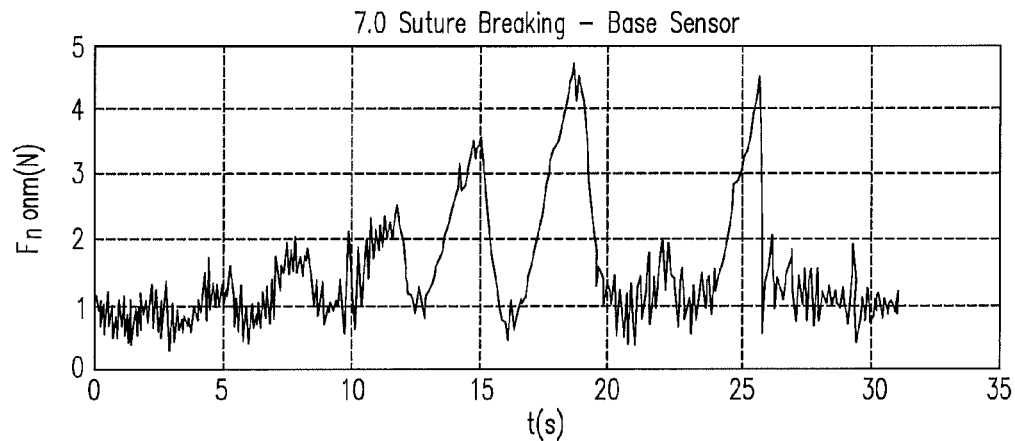
FIG. 24 illustrates force readings from the manipulator of the present invention including a base-mounted force sensor when the manipulator of the present invention provides a continuum of varying forces prior to breaking a suture.

FIGS. 23 and 24 illustrate force readings from the manipulator of the present invention when the manipulator of the present invention tensions and then breaks a suture. Disturbances sensed by the manipulator are clearly provided. FIG. 23 illustrates the results when one end of a 7-0 suture was wound several times around the shaft of an instrument near the wrist and the other end of the suture was wound around the barrel of a ball point pen. A force was then applied manually until the suture snapped (in this case around 6 seconds). This test was performed in free space. FIG. 24 illustrates the results when a 7-0 Prolene suture was held as above and the tension was increased and released to successive higher levels until the suture broke (in this case around 26 seconds).

Figure 25:
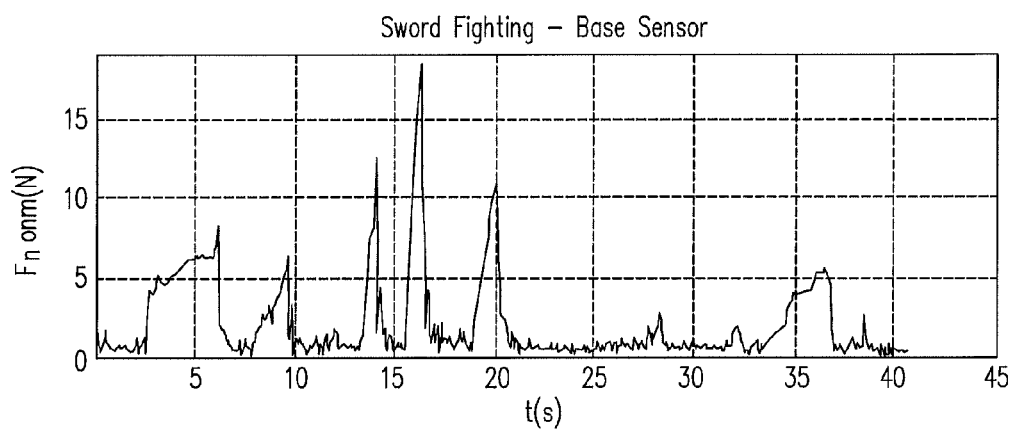
FIG. 25 illustrates force readings from the manipulator of the present invention including a base-mounted force sensor when the instrument of the manipulator of the present invention hits the instrument of another manipulator.

FIG. 25 illustrates force readings from the manipulator of the present invention when an instrument mounted on a manipulator of the present invention hits another instrument mounted on a manipulator internally within an operating environment. Disturbances from approximately 5 N to 18 N sensed by the manipulator are clearly provided.

Advantageously, the present invention provides for sensing external forces applied to a surgical robot arm independent of forces internal to the robotic mechanism (e.g., internal friction, friction between the instrument and the cannula, etc.). The present invention further eliminates undesirable interference from instrument wrist actuator cable tensions and wrist actuation moments by having the sensor outside the patient body on a non-removable, non-sterile part of the surgical robot. Also, not requiring wires or optic fibers to pass through the instrument avoids possible signal loss, breakage of wires or fibers, interfering noise, and/or current leakage while insuring greater reliability and simpler less expensive construction.

Accordingly, the present invention provides information related to (1) the interaction of the instrument tip with the internal patient anatomy and with other surgical instruments, and (2) the interaction of the robotic arm outside the body with the environment including the patient anatomy, the surgical staff, the operating table, and other robotic arms. In one example, this information also may be used to increase the backdrivability of the robotic arm and linkages during manual positioning (clutch mode).

Embodiments described above illustrate but do not limit the invention. It should also be understood that numerous modifications and variations are possible in accordance with the principles of the present invention. Accordingly, the scope of the invention is defined only by the following claims.

We claim:

1. A robotic surgical system, comprising:
   a fixable setup linkage arm comprising a proximal link, a joint coupled to the proximal link, a distal link coupled to the joint, and a free end distal to the joint;
   a servo-driven manipulator arm comprising a base coupled to the free end of the fixable setup linkage arm distal to the distal link of the fixable setup linkage arm, wherein the base is a proximal end of the servo-driven manipulator arm;
   a force and torque (F/T) sensor operably coupled between the free end of the fixable setup linkage arm and the base of the servo-driven manipulator arm, wherein the F/T sensor comprises: a housing operably coupled to the fixable setup linkage arm, an internal hub operably coupled to the servo-driven manipulator arm, a strut, a strain gauge, and a spring counterbalance positioned between the housing and the internal hub,
     the housing comprising a proximal end, a distal end, and a lengthwise axis, the proximal end of the housing being operably coupled to the fixable setup linkage arm, the lengthwise axis of the housing extending between the proximal and distal ends of the housing,
     the internal hub comprising a proximal end, a distal end, a sidewall, and a lengthwise axis, the sidewall connecting the proximal end of the internal hub to the distal end of the internal hub, the distal end of the internal hub being operably coupled to the base of the servo-driven manipulator arm, the lengthwise axis of the internal hub extending between the proximal and distal ends of the internal hub, the lengthwise axis of the housing extending in a same direction as the lengthwise axis of the internal hub, the internal hub being positioned within the housing,
     the spring counterbalance extending from an inner wall of the housing to an exterior surface of the sidewall of the internal hub, the spring counterbalance comprising a first end, a second end, and a lengthwise axis, the first end of the spring counterbalance contacting the inner wall of the housing, the second end of the spring counterbalance contacting the exterior surface of the sidewall of the internal hub, and the lengthwise axis of the spring counterbalance extending between the first and second ends of the spring counterbalance, wherein the spring counterbalance is configured to counteract weight of the servo-driven manipulator arm and an overhanging load moment of the servo-driven manipulator arm, and wherein the lengthwise axis of the spring counterbalance intersects the lengthwise axis of the internal hub,
     the strut extending from the inner wall of the housing to the exterior surface of the sidewall of the internal hub, and
     the strain gauge being mounted on the strut;
   an F/T sensor interface operably coupled to the F/T sensor for decoding signals from the F/T sensor; and
   a master control assembly including one or more masters, wherein at least one or more of the one or more masters is configured to control the servo-driven manipulator arm, wherein information from the F/T sensor is provided to a user of the robotic surgical system through the master control assembly.

2. The system of claim 1, wherein the base of the servo-driven manipulator arm is a location from which at least three degrees of freedom for the servo-driven manipulator arm are provided.

3. The system of claim 1, wherein the servo-driven manipulator arm includes an insertion axis having a base link and a carriage link movably coupled to the base link along a lengthwise axis, the carriage link including an instrument mechanical interface.

4. The system of claim 3, wherein the instrument mechanical interface is configured to mount an instrument including a plurality of strain gauges on a distal end of an instrument shaft.

5. The system of claim 4, wherein the plurality of strain gauges are operably couplable to an instrument signal interface, and the instrument signal interface is configurable to decode signals from the plurality of strain gauges.

6. The system of claim 1, wherein the fixable setup linkage arm is passive or motorized.

7. The system of claim 1, wherein the F/T sensor includes a mechanical interface and an electrical connector interface that operably couple to the fixable setup linkage arm on a first side of the F/T sensor and to the servo-driven manipulator arm on a second side of the F/T sensor.

8. The system of claim 7, wherein the mechanical interface includes sliding engagement means and the electrical connector interface includes D-type connectors.

9. The system of claim 7, wherein an electrical connector interface on a first side of the F/T sensor is electrically coupled to an electrical connector interface on a second side of the F/T sensor by a wire routed around or through a main body of the F/T sensor.

10. The system of claim 7, wherein the electrical connector interface includes a serial bus through which the F/T sensor provides signals to the F/T sensor interface.

11. The system of claim 1, further comprising:
    a surgical instrument operably coupled to a distal end of the servo-driven manipulator arm.

12. The system of claim 11, wherein the base of the servo-driven manipulator arm is a location from which at least three degrees of freedom for the surgical instrument are provided.

13. The system of claim 11, wherein the servo-driven manipulator arm includes an insertion axis having a base link and a carriage link movably coupled to the base link along a lengthwise axis, the carriage link including an instrument interface.

14. The system of claim 13, wherein the surgical instrument is mounted to the instrument interface, the surgical instrument including a plurality of strain gauges on a distal end of an instrument shaft.

15. The system of claim 14, wherein the plurality of strain gauges is operably coupled to an instrument signal interface, and the instrument signal interface is configured to decode signals from the plurality of strain gauges.

16. The system of claim 11, further comprising a sterile drape between the F/T sensor and the surgical instrument, the drape separating a non-sterile part of the robotic surgical system from a sterile surgical field.

17. A method of operating a robotic surgical system, comprising:
  sensing a force on a surgical instrument,
    wherein the sensing uses a force and torque (F/T) sensor operably coupled between a free end of a fixable setup linkage arm of the robotic surgical system and a base of a servo-driven manipulator arm of the robotic surgical system,
    wherein the F/T sensor comprises: a housing operably coupled to the fixable setup linkage arm, an internal hub operably coupled to the servo-driven manipulator arm, a strut, a strain gauge, and a spring counterbalance positioned between the housing and the internal hub,
      the housing comprising a proximal end, a distal end, and a lengthwise axis, the proximal end of the housing being operably coupled to the free end of the fixable setup linkage arm, the lengthwise axis of the housing extending between the proximal and distal ends of the housing,
      the internal hub comprising a proximal end, a distal end, a sidewall, and a lengthwise axis, the sidewall connecting the proximal end of the internal hub to the distal end of the internal hub, the distal end of the internal hub being operably coupled to the base of the servo-driven manipulator arm, the lengthwise axis of the internal hub extending between the proximal and distal ends of the internal hub, the lengthwise axis of the housing extending in a same direction as the lengthwise axis of the internal hub, the internal hub being positioned within the housing,
      the spring counterbalance extending from an inner wall of the housing to an exterior surface of the sidewall of the internal hub, the spring counterbalance comprising a first end, a second end, and a lengthwise axis, the first end of the spring counterbalance contacting the inner wall of the housing, the second end of the spring counterbalance contacting the exterior surface of the sidewall of the internal hub, and the lengthwise axis of the spring counterbalance extending between the first and second ends of the spring counterbalance, wherein the spring counterbalance is configured to counteract weight of the servo-driven manipulator arm and an overhanging load moment of the servo-driven manipulator arm, and wherein the lengthwise axis of the spring counterbalance intersects the lengthwise axis of the internal hub,
      the strut extending from the inner wall of the housing to the exterior surface of the sidewall of the internal hub, and
      the strain gauge being mounted on the strut,
    wherein the surgical instrument is mounted to a distal end of the servo-driven manipulator arm,
    wherein the fixable setup linkage arm comprises a proximal link, a joint coupled to the proximal link, a distal link coupled to the joint, and the free end distal to the joint,
    and
    wherein the base is a proximal end of the servo-driven manipulator arm;
  passing signals from the F/T sensor to an interface operably coupled to the F/T sensor, wherein the interface decodes the signals from the F/T sensor; and
  passing information from the F/T sensor to a master control assembly to provide a user of the robotic surgical system feedback through the master control assembly, wherein the master control assembly includes one or more masters for controlling the servo-driven manipulator arm.

18. The method of claim 17, wherein the sensed force on the surgical instrument is one of an interaction of the surgical instrument with an internal patient anatomy, and an interaction of the surgical instrument with another surgical instrument.

19. The method of claim 17, wherein the sensed force on the surgical instrument is one of suture tension, a collision with another surgical instrument, tissue dissection, retraction, and palpation.

20. The method of claim 17, further comprising increasing backdrivability of the servo-driven manipulator arm during manual positioning using data from the F/T sensor.

21. The method of claim 17, further comprising using a notch filter on a signal from the F/T sensor.

22. The method of claim 17, further comprising using a low-pass filter on a signal from the F/T sensor to reduce F/T sensor noise.

23. The method of claim 17, further comprising applying a threshold to a signal from the F/T sensor to eliminate forces at or below a F/T sensor noise level.

24. The method of claim 17, further comprising applying a variable gain on a signal from the F/T sensor to attenuate or strengthen the sensed force, wherein the variable gain is inversely dependent on a surgical instrument tip velocity or a servo-driven manipulator arm velocity.

25. The method of claim 17, further comprising draping the servo-driven manipulator arm with a sterile drape such that the surgical instrument is on a sterile side of the drape and the F/T sensor is on a non-sterile side of the drape.

26. The method of claim 17, further comprising:
  sensing an axial force along a lengthwise axis of an instrument shaft of the surgical instrument,
    wherein the sensing the axial force uses the F/T sensor, and
    wherein the surgical instrument includes a plurality of strain gauges on a distal end of the instrument shaft; and
  sensing side forces on the surgical instrument using the plurality of strain gauges.

27. The method of claim 17, further comprising distinguishing between forces on the servo-driven manipulator arm which are internal and external to a patient body based upon a magnitude of a signal from the F/T sensor.

* * * * *